US009708908B2

(12) United States Patent
Gao et al.

(10) Patent No.: US 9,708,908 B2
(45) Date of Patent: Jul. 18, 2017

(54) INTEGRATED COMPUTATIONAL ELEMENT WITH MULTIPLE FREQUENCY SELECTIVE SURFACES

(71) Applicant: HALLIBURTON ENERGY SERVICES, INC., Houston, TX (US)

(72) Inventors: Li Gao, Katy, TX (US); Michael T. Pelletier, Houston, TX (US); David L. Perkins, The Woodlands, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 0 days.

(21) Appl. No.: 14/762,194

(22) PCT Filed: Jun. 13, 2014

(86) PCT No.: PCT/US2014/042368
§ 371 (c)(1),
(2) Date: Jul. 20, 2015

(87) PCT Pub. No.: WO2015/191084
PCT Pub. Date: Dec. 17, 2015

(65) Prior Publication Data
US 2016/0265352 A1    Sep. 15, 2016

(51) Int. Cl.
| | |
|---|---|
| *E21B 49/08* | (2006.01) |
| *E21B 47/10* | (2012.01) |
| *G01B 11/25* | (2006.01) |
| *G01N 21/01* | (2006.01) |
| *G01J 3/00* | (2006.01) |

(Continued)

(52) U.S. Cl.
CPC .............. *E21B 49/08* (2013.01); *E21B 47/10* (2013.01); *G01B 11/25* (2013.01); *G01J 3/00* (2013.01); *G01N 21/01* (2013.01); *G01N 21/31* (2013.01); *G02B 27/60* (2013.01); *H05K 1/0296* (2013.01); *H05K 1/09* (2013.01); *H05K 3/125* (2013.01);

(Continued)

(58) Field of Classification Search
CPC ...... E21B 49/08; G01N 21/31; H05K 1/0296; G02F 1/153
See application file for complete search history.

(56) References Cited

U.S. PATENT DOCUMENTS

| | | |
|---|---|---|
| 5,075,550 A | 12/1991 | Miller et al. |
| 5,399,229 A | 3/1995 | Stefani et al. |

(Continued)

FOREIGN PATENT DOCUMENTS

| | | |
|---|---|---|
| EP | 1969326 | 9/2008 |
| EP | 2087328 | 8/2009 |

(Continued)

OTHER PUBLICATIONS

Authorized officer Ahn, Jae Yul, International Search Report and Written Opinion for PCT/US2013/049697, mailed Apr. 11, 2014, 11 pages.

(Continued)

*Primary Examiner* — Casey Bryant
(74) *Attorney, Agent, or Firm* — Benjamin Fite; Parker Justiss, P.C.

(57) ABSTRACT

An optical analysis tool includes an integrated computational element (ICE). The ICE includes a plurality of layers stacked along a first axis. Constitutive materials of the layers are electrically conductive and patterned with corresponding patterns. An arrangement of the patterns with respect to each other is related to a characteristic of a sample.

33 Claims, 8 Drawing Sheets

(51) Int. Cl.
*G01N 21/31* (2006.01)
*H05K 1/02* (2006.01)
*H05K 1/09* (2006.01)
*H05K 3/12* (2006.01)
*G02B 27/60* (2006.01)

(52) U.S. Cl.
CPC ... *H05K 3/1275* (2013.01); *H05K 2201/0323* (2013.01); *H05K 2201/0329* (2013.01)

(56) References Cited

U.S. PATENT DOCUMENTS

| | | |
|---|---|---|
| 5,453,716 A | 9/1995 | Person et al. |
| 5,537,479 A | 7/1996 | Kreisel et al. |
| 5,619,366 A | 4/1997 | Rhoads et al. |
| 6,078,389 A | 6/2000 | Zetter |
| 6,154,550 A | 11/2000 | Beyer |
| 6,163,259 A | 12/2000 | Barsumian et al. |
| 6,198,531 B1 | 3/2001 | Myrick et al. |
| 6,213,250 B1 | 4/2001 | Wisniewski et al. |
| 6,218,978 B1 | 4/2001 | Simpkin et al. |
| 6,529,276 B1 | 3/2003 | Myrick |
| 6,646,753 B2 | 11/2003 | Zhang et al. |
| 6,744,517 B1 | 6/2004 | Forno et al. |
| 6,804,060 B1 | 10/2004 | Tsai et al. |
| 6,905,578 B1 | 6/2005 | Moslehi et al. |
| 6,965,431 B2 | 11/2005 | Vo-Dinh et al. |
| 7,123,844 B2 | 10/2006 | Myrick |
| 7,138,156 B1 | 11/2006 | Myrick et al. |
| 7,163,901 B2 | 1/2007 | Downey |
| 7,332,044 B2 | 2/2008 | Sidorin et al. |
| 7,332,094 B2 | 2/2008 | Abney et al. |
| 7,472,748 B2 | 1/2009 | Gdanski et al. |
| 7,623,233 B2 | 11/2009 | Freese et al. |
| 7,679,563 B2 | 3/2010 | Werner et al. |
| 7,697,141 B2 | 4/2010 | Jones et al. |
| 7,712,527 B2 | 5/2010 | Roddy |
| 7,753,847 B2 | 7/2010 | Greenleaf et al. |
| 7,777,870 B2 | 8/2010 | Hayes et al. |
| 7,792,644 B2 | 9/2010 | Kotter et al. |
| 7,828,929 B2 | 11/2010 | Lee et al. |
| 7,834,999 B2 | 11/2010 | Myrick et al. |
| 7,911,605 B2 | 3/2011 | Myrick et al. |
| 7,920,258 B2 | 4/2011 | Myrick et al. |
| 7,934,556 B2 | 5/2011 | Clark et al. |
| 8,054,212 B1 | 11/2011 | Holly et al. |
| 8,106,850 B1 | 1/2012 | Gregoire et al. |
| 8,141,633 B2 | 3/2012 | Hampton et al. |
| 8,164,061 B2 | 4/2012 | Pawlak et al. |
| 8,216,161 B2 | 7/2012 | Darlington et al. |
| 8,252,112 B2 | 8/2012 | Ovshinsky |
| 2004/0233508 A1 | 11/2004 | Kosc |
| 2005/0054928 A1 | 3/2005 | Cerofolini |
| 2007/0282647 A1 | 12/2007 | Freese et al. |
| 2008/0231849 A1 | 9/2008 | Myrick et al. |
| 2008/0238801 A1 | 10/2008 | Ragan |
| 2008/0276687 A1 | 11/2008 | Myrick et al. |
| 2009/0073433 A1 | 3/2009 | Myrick et al. |
| 2009/0097024 A1 | 4/2009 | Blackburn et al. |
| 2009/0140144 A1 | 6/2009 | Myrick et al. |
| 2009/0154288 A1 | 6/2009 | Heathman |
| 2009/0182693 A1 | 7/2009 | Fulton et al. |
| 2009/0216504 A1 | 8/2009 | Priore et al. |
| 2009/0219512 A1 | 9/2009 | Myrick et al. |
| 2009/0219538 A1 | 9/2009 | Myrick et al. |
| 2009/0219539 A1 | 9/2009 | Myrick et al. |
| 2009/0250613 A1 | 10/2009 | Myrick et al. |
| 2009/0299946 A1 | 12/2009 | Myrick et al. |
| 2009/0316150 A1 | 12/2009 | Myrick et al. |
| 2010/0050905 A1 | 3/2010 | Lewis et al. |
| 2010/0051266 A1 | 3/2010 | Roddy et al. |
| 2010/0051275 A1 | 3/2010 | Lewis et al. |
| 2010/0073666 A1 | 3/2010 | Perkins et al. |
| 2010/0141952 A1 | 6/2010 | Myrick et al. |
| 2010/0149537 A1 | 6/2010 | Myrick et al. |
| 2010/0153048 A1 | 6/2010 | Myrick et al. |
| 2010/0182600 A1 | 7/2010 | Freese et al. |
| 2010/0195105 A1 | 8/2010 | Myrick et al. |
| 2010/0238801 A1 | 9/2010 | Smith et al. |
| 2010/0245096 A1 | 9/2010 | Jones et al. |
| 2010/0265509 A1 | 10/2010 | Jones et al. |
| 2010/0271285 A1 | 10/2010 | Yun et al. |
| 2010/0302539 A1 | 12/2010 | Myrick et al. |
| 2010/0305741 A1 | 12/2010 | Myrick |
| 2010/0328669 A1 | 12/2010 | Myrick et al. |
| 2011/0048708 A1 | 3/2011 | Glasbergen et al. |
| 2011/0093205 A1 | 4/2011 | Bern |
| 2011/0163046 A1 | 7/2011 | Neal et al. |
| 2011/0199610 A1 | 8/2011 | Myrick et al. |
| 2012/0268744 A1 | 10/2012 | Wolf et al. |
| 2013/0284894 A1 | 10/2013 | Freese et al. |
| 2013/0284895 A1 | 10/2013 | Freese et al. |
| 2013/0284896 A1 | 10/2013 | Freese et al. |
| 2013/0284897 A1 | 10/2013 | Freese et al. |
| 2013/0284898 A1 | 10/2013 | Freese et al. |
| 2013/0284899 A1 | 10/2013 | Freese et al. |
| 2013/0284900 A1 | 10/2013 | Freese et al. |
| 2013/0284901 A1 | 10/2013 | Freese et al. |
| 2013/0284904 A1 | 10/2013 | Freese et al. |
| 2013/0286398 A1 | 10/2013 | Freese et al. |
| 2013/0286399 A1 | 10/2013 | Freese et al. |
| 2013/0287061 A1 | 10/2013 | Freese et al. |

FOREIGN PATENT DOCUMENTS

| | | |
|---|---|---|
| EP | 2140238 | 1/2010 |
| KR | 10-2011-0075539 | 7/2011 |
| KR | 2013/0017718 | 2/2013 |
| WO | WO 2004/015364 | 2/2004 |
| WO | WO 2005/093904 | 10/2005 |
| WO | WO 2006/031733 | 3/2006 |
| WO | WO 2006/137902 | 12/2006 |
| WO | WO 2007/064575 | 6/2007 |
| WO | WO 2007/015115 | 8/2007 |
| WO | WO2011/103066 | 8/2011 |
| WO | WO2013/022556 | 2/2013 |
| WO | WO2014/042642 | 3/2014 |

OTHER PUBLICATIONS

Authorized officer Cha, Young Lan, International Search Report and Written Opinion for PCT/US2013/049693, mailed Mar. 20, 2014, 12 pages.

Commissioner, International Search Report and Written Opinion for PCT/US2014/042368, mailed Mar. 13, 2015, 15 pages.

Gdanski et al., "Using Lines-of-Solutions to Understand Fracture Conductivity and Fracture Cleanup," SPE 142096, SPE Production and Operations Symposium held in Oklahoma City, OK, Mar. 27-29, 2011, 16 pages.

Telemark, "Model 820 In-Situ Spectroscopic Optical Monitor," Dec. 2010, 4 pages.

J.A. Woollam Co., Inc., Characterizing Processes with EASE® In Situ Applications, Application Note, 2009, 3 pages.

Gdanski et al., "A New Model for Matching Fracturing Fluid Flowback Composition," SPE Hydraulic Fracturing Technology Conference held in College Station, Texas, SPE 106040, Jan. 29-31, 2007, 9 pages.

Bossard et al., "The Design and fabrication of planar multiband metallodielectric frequency selective surfaces for infrared applications", IEEE Trans. on Antennas and Propagation, v. 50, No. 4, Apr. 2006, 12 pages.

Frey et al., "Temperature-dependent refractive index of silicon and germanium," NASA Goddard Space Flight Center, Greenbelt, MD, 2006, 10 pages.

Zoeller et al., "Substantial progress in optical monitoring by intermittent measurement technique," SPIE, Published in the processing of the OSD, Jena 2005, vol. 5963-13, 9 pages.

Haibach et al., "Precision in multivariate optical computing," Applied Optics, vol. 43, No. 10, Apr. 1, 2004, 11 pages.

(56) References Cited

OTHER PUBLICATIONS

Rabady et al., "High-resolution photometric optical monitoring for thin-film deposition," Applied Optics, Optical Society of America, vol. 43, No. 1, Jan. 1, 2004, 6 pages.

Priore et al., "Novel Imaging Systems: Multivariate Optical Computing in the UV-VIS," Department of Chemistry and Biochemistry, University of South Carolina, 2003, 5 pages.

Myrick et al., "A single-element all-optical approach to chemometric prediction," Vibrational Spectroscopy 28, 2002, 9 pages.

Myrick, "Multivariate optical elements simplify spectroscopy," Laser Focus World, Mar. 1, 2002, access date Feb. 28, 2013, 3 pages http://www.laserfocusworld.com/articles/print/volume-38/issue3/features/spectroscopy/multivariate-optical-elements-simplify-spectroscopy.html.

Myrick et al., "Application of multivariate optical computing to simple near-infrared point measurements," SPIE vol. 4574, Department of Chemistry and biochemistry, University of South Carolina, 2002, 8 pages.

Morton et al., "Optical Monitoring of Thin-films Using Spectroscopic Ellipsometry," Society of Vacuum Coaters, 45th Annual Technical Conference Proceedings, 2002, 7 pages.

Paul et al., "Fabrication of mid-infrared frequency-selective surfaces by soft lithography", Applied Optics, v. 40, No. 25, Sep. 2001, 5 pages.

Myrick et al., "Spectral Tolerance Determination for Multivariate Optical Element Design," Fresenuis' Journal of Analytical Chemistry, 369, 2001, 5 pages.

Eastwood et al., "Filed applications of stand-off sensing using visible/NIR multivariate optical computing," Department of Chemistry and Biochemistry, University of South Carolina, SPE vol. 4199, 2001, 10 pages.

Soyemi et al., "Novel Filter Design Algorithm for Multivariate Optical Computing," Advanced Environmental and Chemical Sensing Technology, SPIE vol. 4205, 2001, 12 pages.

Munk, "Frequency Selective Surfaces: Theory and Design", John Wiley and Sons, Inc., New York, 2000, 92 pages.

Woollam et al., "Overview of Variable Angle Spectroscopic Ellipsometer (VASE), Part 1: Basic Theory and Typical Applications," Society of Photo-Optical Instrumentation Engineers, Critical Reviews of Optical Science Technology CR72, 1999, 28 pages.

Wu, "Frequency Selective Surface and Grid Array", TRW Electronic Systems and Technology Division, John Wiley & Sons, Inc., New York, 1995, 10 pages.

Nelson et al., "Multivariate Optical Computation for Predictive Spectroscopy", Analytical Chemistry 1998, 70, 10 pages.

Grader et al., "Fourier transform infrared spectroscopy of a single aerosol particle," J. Chem. Phys. 86 (11), Jun. 1, 1987, 7 pages.

Li, "Refractive Index of Silicon and Germanium and Its Wavelength and Temperature Derivatives," Center for Information and Numerical Data Analysis and Synthesis, Purdue University, J. Phys. Chem. Ref. Data, vol. 9, No. 3, 1980, 98 pages.

INTEGRATED COMPUTATIONAL ELEMENT WITH MULTIPLE FREQUENCY SELECTIVE SURFACES

CLAIM OF PRIORITY

This application is a U.S. National Stage of International Application No. PCT/US/2014/042368, filed Jun. 13, 2014.

BACKGROUND

The subject matter of this disclosure is generally related to optical analysis systems for analyzing a substance of interest, for example, crude petroleum, gas, water, or other wellbore fluids. For instance, the disclosed optical analysis systems use an integrated computational element (ICE) that includes multiple frequency selective surfaces.

Information about a substance can be derived through the interaction of light with that substance. The interaction changes characteristics of the light, for instance the frequency (and corresponding wavelength), intensity, polarization, and/or direction (e.g., through scattering, absorption, reflection or refraction). Chemical, thermal, physical, mechanical, optical or various other characteristics of the substance can be determined based on the changes in the characteristics of the light interacting with the substance. As such, in certain applications, one or more characteristics of crude petroleum, gas, water, or other wellbore fluids can be derived in-situ, e.g., downhole at well sites, as a result of the interaction between these substances and light.

Some conventional ICEs include an electrically conductive layer (e.g., made from Au, Al, etc.) that is lithographically patterned on a substrate. The patterned layer includes identical features arranged in an array on a surface of the substrate, where the features include one or more geometric shapes, e.g., polygons such as triangles, quadrilaterals, hexagons, or circles, etc. The layer patterned in this manner represents a frequency selective surface (FSS) that causes an ICE to selectively transmit or reflect, during operation of the ICE, light in at least a portion of a particular wavelength range by differing amounts, such that the differing amounts are related to one or more chemical or physical characteristics of a sample. The ICE measures values of the various sample characteristics through the use of regression techniques over the particular wavelength range.

Because ICEs passively extract information from the light modified by a sample, they can be incorporated in low cost and rugged optical analysis tools. Hence, ICE-based downhole optical analysis tools can provide a relatively low cost, rugged and accurate system for monitoring quality of wellbore fluids, for instance.

DESCRIPTION OF DRAWINGS

Like reference symbols in the various drawings indicate like elements.

DETAILED DESCRIPTION

Figure 1:
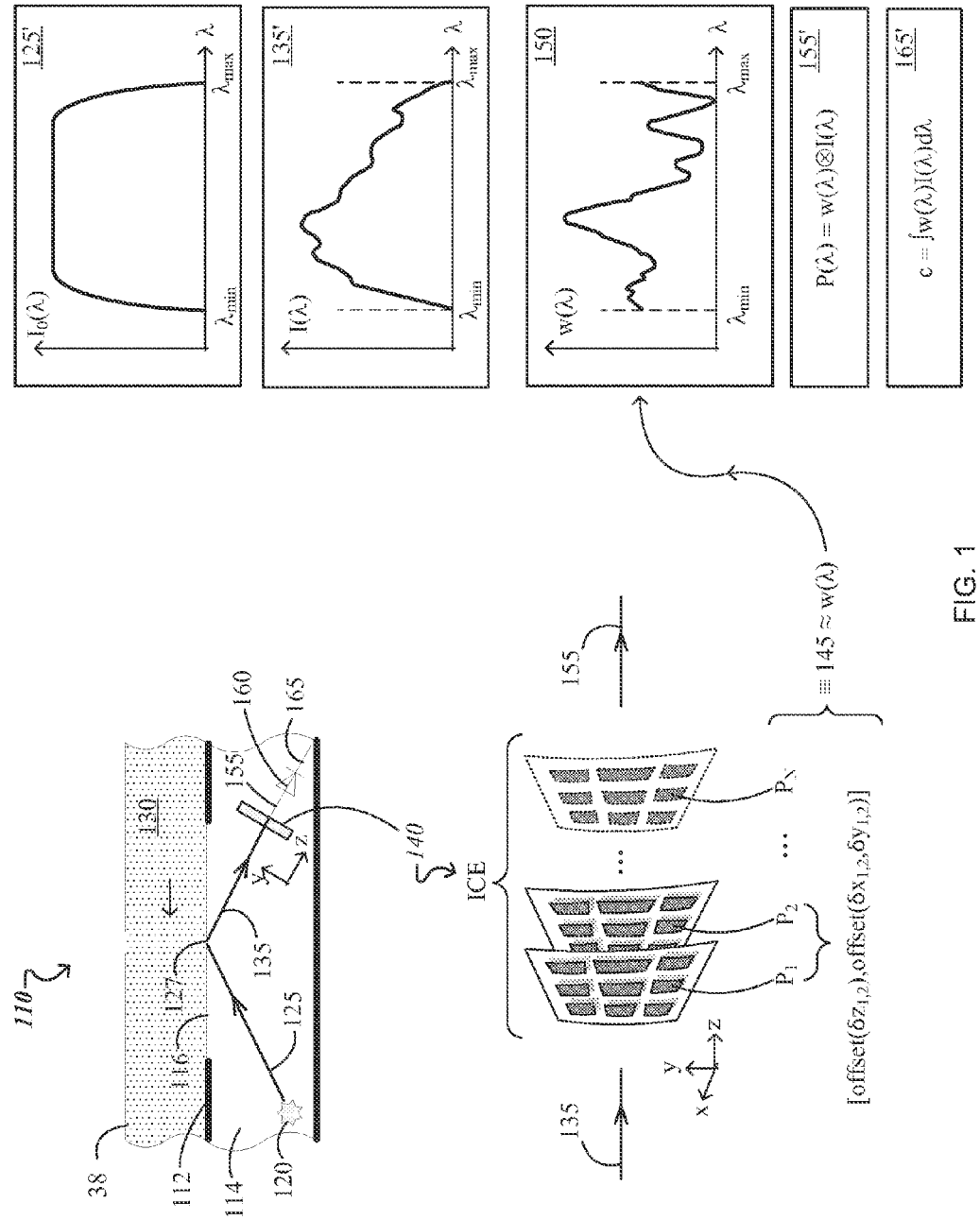
FIG. 1 shows an example of an optical analysis tool for measuring a property of a sample using an ICE that contains multiple frequency selective surfaces.

In accordance with the disclosed technologies, optical analysis systems use an integrated computational element (ICE) including multiple frequency selective surfaces (FSS) stacked along a first axis, such that an arrangement of the frequency selective surfaces with respect to each other is related to a physical or chemical characteristic of a sample. The frequency selective surfaces are respective layers of electrically conductive materials patterned with corresponding patterns.

In some implementations, the frequency selective surfaces of the ICE are respective two or more layers of electrically conductive materials patterned with corresponding patterns. Here, the arrangement of the frequency selective surfaces with respect to each other includes a lateral offset of the respective patterned layers in a plane perpendicular to the first axis, such that the lateral offset causes a Moiré pattern that is related to the characteristic of the sample. For example, the lateral offset that causes the Moiré pattern can be a translation in the plane perpendicular to the first axis. As another example, the lateral offset that causes the Moiré pattern can be a rotation in the plane perpendicular to the first axis. In other implementations, the frequency selective surfaces of the ICE are at least three respective layers of electrically conductive materials patterned with corresponding patterns. Here, the arrangement of the frequency selective surfaces with respect to each other has translational symmetry along the first axis to form a three dimensional (3D) lattice of the patterned layers, such that the 3D lattice is related to the characteristic of the sample.

More specifically, regardless of whether the arrangement of frequency selective surfaces includes frequency selective surfaces that are offset in-plane or frequency selective surfaces that are offset out-of-plane, the arrangement of frequency selective surfaces causes the ICE to selectively transmit or reflect, during operation of the optical analysis systems, light in at least a portion of a wavelength range $[\lambda_{min}, \lambda_{max}]$ by differing amounts, the differing amounts being related to the characteristic of the sample.

The above noted Moiré pattern or 3D lattice of patterns, either of which corresponds—over a wavelength range $[\lambda_{min}, \lambda_{max}]$—to the characteristic of the sample with a desired accuracy, can be obtained by generating an arrangement of frequency selective surfaces having a relatively simple pattern and being appropriately offset in-plane or out-of-plane relative to each other. In contrast, in order for a single FSS to correspond—over the wavelength range $[\lambda_{min}, \lambda_{max}]$—to the characteristic of the sample with the desired accuracy, the single FSS typically requires a relatively complex pattern. Moreover, changing the in-plane or out-of-plane offset of the frequency selective surfaces in accordance with the disclosed technologies can cause an adjustment of the correspondence between the arrangement of the frequency selective surfaces and the characteristic of the sample.

Further, the electrically conductive patterns of the frequency selective surfaces disclosed herein can be printed on one or more substrates (e.g., sheet films) of the ICE using electrically conductive inks. The printing can be inexpensively performed with high resolution inkjet printers or with a micro-stamp.

Furthermore, printing of the FSS in accordance with the disclosed technologies can be used to create ICEs for operation at lower frequencies (or equivalently longer wavelengths) over which conventional ICE technology is typically non-operational. Conventional FSS-based ICEs are typically designed to operate over near-infrared to relatively short infrared wavelengths, while the disclosed FSS-based ICEs are designed to operate over an extended wavelength range from infrared to microwave. In this manner, FSS-based ICE technologies can be extended into the functional group region of the IR spectrum and beyond. Applications made possible by the disclosed technologies include detecting of water vapor in a process environment, and/or monitoring $CO_2$ levels.

Prior to describing example implementations of ICEs that contain a combination of frequency selective surfaces, optical analysis tools based on the disclosed ICEs are described below along with examples of their use in oil/gas exploration.

FIG. 1 shows an example of an optical analysis tool 110 for measuring a characteristic of a sample 130 using an ICE 140 that contains multiple frequency selective surfaces. In this example, the optical analysis tool 110 includes a light source 120, the ICE 140 that contains the multiple frequency selective surfaces and an optical transducer 160. The optical analysis tool 110 has a frame 112 such that the foregoing components are arranged in an enclosure 114 thereof. A cross-section of the optical analysis tool 110 in a plane perpendicular to the page can vary, depending on the space available. For example, the optical analysis tool's cross-section can be circular or rectangular, for instance. The optical analysis tool 110 directs light to a sample 130 through an optical interface 116, e.g., a window in the frame 112. The optical analysis tool 110 is configured to probe the sample 130 (e.g., wellbore fluids stationary or flowing) in a wellbore 38 through the optical interface 116 and to determine an amount (e.g., a value) of a given characteristic (also referred to as a property to be measured) of the probed sample 130. The property to be measured can be any one of multiple properties of the sample 130 including concentration of a given substance in the sample, a gas-oil-ratio (GOR), pH value, density, viscosity, etc.

The light source 120 outputs light with a source spectrum $I_0(\lambda)$ 125' over a particular wavelength range $[\lambda_{min},\lambda_{max}]$. In some cases, the source spectrum $I_0(\lambda)$ 125' has non-zero intensity over the entire or most of the particular wavelength range $[\lambda_{min},\lambda_{max}]$. In some implementations of the disclosed technologies, the source spectrum $I_0(\lambda)$ 125' extends through an IR (2.5-200 μm) spectral range. In some implementations of the disclosed technologies, the source spectrum further extends through a microwave (0.2-10 mm) spectral range. In some implementations of the disclosed technologies, the light source 120 is tunable and is configured in combination with time resolved signal detection and processing.

The light source 120 is arranged to direct a probe beam 125 of the source light towards the optical interface 116 where it illuminates the sample 130 at a location 127. The source light in the probe beam 125 interacts with the sample 130 and reflects off it as light modified by the sample 130. The sample modified light 135 has a modified spectrum $I(\lambda)$ 135' over the particular wavelength range. In general, the modified spectrum $I(\lambda)$ 135' encodes information about multiple characteristics associated with the sample 130, and more specifically the encoded information relates to current values of the multiple characteristics. In the example illustrated in FIG. 1, the modified spectrum 135' contains information about one or more characteristics of the wellbore fluids 130.

With continued reference to FIG. 1, and the Cartesian coordinate system provided therein for reference, an ICE 140 that contains multiple frequency selective surfaces is arranged to receive a beam 135 of the sample modified light, and is configured to process it and to output a beam 155 of processed light. The beam 135 of sample modified light is incident along the z-axis on an input optical interface of the ICE 140 that contains multiple frequency selective surfaces, and the beam 155 of processed light is output along the z-axis—after transmission through the ICE 140 that contains multiple frequency selective surfaces—at an output interface thereof. In this example, the multiple frequency selective surfaces are stacked along the z-axis.

An arrangement 145 of the multiple frequency selective surfaces causes the ICE 140 to processes the sample modified light 135 by weighting it in accordance with an optical spectrum $w(\lambda)$ 150 associated, over a wavelength range $[\lambda_{min},\lambda_{max}]$, with a characteristic to be measured. In some implementations, not explicitly illustrated in FIG. 1, the ICE 140 that contains multiple frequency selective surfaces further contains one or more filters to block light shorter than $\lambda_{min}$ and longer than $\lambda_{max}$, such that processed light 155 output by the ICE 140 that contains the multiple frequency selective surfaces is limited to the wavelength range $[\lambda_{min}, \lambda_{max}]$ over which the optical spectrum $w(\lambda)$ 150 is associated with the characteristic to be measured.

The optical spectrum $w(\lambda)$ 150 is determined offline by applying conventional processes to a set of calibration spectra $I(\lambda)$ of the sample which correspond to respective known values of the characteristic to be measured. As illustrated by optical spectrum $w(\lambda)$ 150, optical spectra generally may include multiple local maxima (peaks) and minima (valleys) between $\lambda_{min}$ and $\lambda_{max}$. The peaks and valleys may have the same or different amplitudes. For instance, an optical spectrum $w(\lambda)$ can be determined through regression analysis of $N_C$ calibration spectra $I_j(\lambda)$ of a sample, where j=1, . . . , $N_C$, such that each of the calibration spectra $I_j(\lambda)$ corresponds to an associated known value of a given characteristic for the sample. A typical number $N_C$ of calibration spectra $I_j(\lambda)$ used to determine the optical spectrum $w(\lambda)$ 150 through such regression analysis can be $N_C$=10, 40 or 100, for instance. The regression analysis outputs, within the $N_C$ calibration spectra $I_j(\lambda)$, a spectral pattern that is unique to the given characteristic. The spectral pattern output by the regression analysis corresponds to the optical spectrum $w(\lambda)$ 150. In this manner, when a value of the given characteristic for the sample is unknown, a modified spectrum $I_U(\lambda)$ of the sample is acquired by interacting the probe beam 125 with the sample 130, then the modified spectrum $I_U(L)$ is weighted by the ICE 140 that contains the multiple frequency selective surfaces to determine a magnitude of the spectral pattern corresponding to the optical spectrum $w(\lambda)$ 150 within the modified spectrum $I_U(\lambda)$. The determined magnitude is proportional to the unknown value of the given characteristic for the sample.

For example, the sample can be a mixture (e.g., the wellbore fluid 130) containing substances X, Y and Z, and the characteristic to be measured for the mixture is concentration $c_X$ of substance X in the mixture. In this case, $N_C$ calibration spectra $I_j(\lambda)$ were acquired for $N_C$ samples of the mixture having respectively known concentration values for each of the substances contained in the $N_C$ samples. By applying regression analysis to the $N_C$ calibration spectra $I_j(\lambda)$, a first spectral pattern that is unique to the concentration $c_X$ of the X substance can be detected (recognized), such that the first spectral pattern corresponds to a first optical spectrum $w_{CX}(\lambda)$ associated with a first ICE 140 that contains multiple frequency selective surfaces, for example. Similarly, second and third spectral patterns that are respectively unique to concentrations $c_Y$ and $c_Z$ of the Y and Z substances can also be detected, such that the second and third spectral patterns respectively correspond to second and third optical spectra $w_{CY}(\lambda)$ and $w_{CZ}(\lambda)$ respectively associated with a second ICE that contains multiple frequency selective surfaces and a third ICE 140 that contains multiple frequency selective surfaces. In this manner, when a new sample of the mixture (e.g., the wellbore fluid 130) has an unknown concentration $c_X$ of the X substance, for instance, a modified spectrum $I_U(\lambda)$ of the new sample can be acquired by interacting the probe beam with the mixture, then the modified spectrum $I_U(\lambda)$ is weighted with the first ICE 140 that contains multiple frequency selective surfaces to determine a magnitude of the first spectral pattern within the modified spectrum $I_U(\lambda)$. The determined magnitude is proportional to the unknown value of the concentration $C_X$ of the X substance for the new sample.

As noted above, the frequency selective surfaces of the ICE 140 are stacked along the z-axis in an arrangement 145 that corresponds or is spectrally equivalent to, over the wavelength range $[\lambda_{min},\lambda_{max}]$, an optical spectrum $w(\lambda)$ 150 associated with the ICE 140. Here, the arrangement 145 of the frequency selective surfaces includes (1) patterns $P_i$ of electrically conductive layers $L_i$ that form the frequency selective surfaces, and where each pattern $P_i$ contains lateral features, e.g., triangular, rectangular, hexagonal or circular, periodically distributed within an associated electrically conductive layer $L_i$, $i=1, \ldots, N \geq 2$; (2) separation $\delta z_{i,i+1}$ between patterns $P_i$, $P_{i+1}$ of adjacent layers $L_i$, $L_{i+1}$ along the z-axis (also referred to as axial offset or out-of-plane offset); and (3) separations $\delta x_{i,i+1}$ and/or $\delta y_{i,i+1}$ between patterns $P_i$, $P_{i+1}$ of the adjacent layers $L_i$, $L_{i+1}$ perpendicular to the z-axis (also referred to as lateral offsets or in-plane offsets.) Various examples of arrangements 145 of the frequency selective surfaces of the ICE 140 are described below in connection with FIGS. 2A-2C and 3.

In this manner, the arrangement 145 of the frequency selective surfaces of the ICE 140 is chosen to be spectrally equivalent, over the wavelength range $[\lambda_{min},\lambda_{max}]$, to the optical spectrum $w(\lambda)$ 150 associated with the characteristic to be measured. In some implementations of the disclosed technologies, the wavelength range $[\lambda_{min},\lambda_{max}]$ over which an arrangement 145 of the frequency selective surfaces of the ICE 140 is spectrally equivalent to the optical spectrum of the ICE extends through an IR (2.5-200 µm) spectral range. In some implementations of the disclosed technologies, the wavelength range $[\lambda_{min},\lambda_{max}]$ over which another arrangement 145 of the frequency selective surfaces of the ICE 140 is spectrally equivalent to the optical spectrum of the ICE extends through a microwave (0.2-10 mm) spectral range.

Contributions of the optical spectrum $w(\lambda)$ associated with the ICE 140 that are from wavelengths outside the wavelength range $[\lambda_{min},\lambda_{max}]$ are removed from the processed light 155, by the one or more band-limiting filters associated with the ICE 140 (not shown in FIG. 1), to reduce analysis noise potentially caused by such "outside-of-band" contributions which may not be spectrally equivalent to the optical spectrum $w(\lambda)$ 150 associated with the characteristic to be measured. In this manner, contributions of the optical spectrum $I(\lambda)$ 135' of the sample modified light that are from wavelengths outside the wavelength range $[\lambda_{min},\lambda_{max}]$ are weighted to zero.

Continuing the description of functional aspects of the optical analysis tool 110, the beam 155 of processed light output by the ICE 140 that contains the multiple frequency selective surfaces has a processed spectrum $P(\lambda)=w(\lambda)\otimes I(\lambda)$ 155' over the wavelength range $[\lambda_{min},\lambda_{max}]$ such that the processed spectrum 155' represents the modified spectrum $I(\lambda)$ 135' weighted by the optical spectrum $w(\lambda)$ 150 associated with the characteristic to be measured.

The beam 155 of processed light is directed from the ICE 140 that contains the multiple frequency selective surfaces to the optical transducer 160, which detects the processed light 155 and outputs a detector signal 165. A value (e.g., a voltage) of the detector signal 165 is a result of an integration of the processed spectrum 155' over the wavelength range $[\lambda_{min},\lambda_{max}]$ and is related to the unknown value "c" 165' of the characteristic to be measured for the sample 130.

In some implementations, the optical analysis tool 110 can include a second ICE that contains multiple frequency selective surfaces (not shown in FIG. 1) associated with a second optical spectrum $w_2(\lambda)$. Here, a second arrangement 145-2 of the frequency selective surfaces of the second ICE 140 is chosen to be spectrally equivalent, over the wavelength range $[\lambda_{min},\lambda_{max}]$, to the optical spectrum $w_2(\lambda)$ associated with a second characteristic to be measured. Hence, a second processed spectrum represents the modified spectrum $I(\lambda)$ 135' weighted by the second optical spectrum $w_2(\lambda)$ over the wavelength range $[\lambda_{min},\lambda_{max}]$, such that a second value of a second detector signal is related to a value of the second characteristic of the sample 130.

In some implementations, the value 165' of the characteristic to be measured can be logged along with a measurement time, geo-location, and other metadata, for instance. In some implementations, the detector signal 165, which is related to a characteristic to be measured by the optical analysis tool 110, can be used as a feedback signal to adjust the characteristic of the sample, to modify the sample or environmental conditions associated with the sample, as desired.

In the example illustrated in FIG. 1, the ICE 140 that contains multiple frequency selective surfaces of the optical analysis tool 110 is described generally as having an arrangement 145 of the frequency selective surfaces. Examples of the arrangement 145 of the frequency selective surfaces of the ICE 140 are described below.

In some implementations, frequency selective surfaces of an ICE are respective two or more layers of electrically conductive materials patterned with corresponding patterns and stacked along the z-axis, for instance. Here, an arrangement of the two or more patterned layers with respect to each other is defined in terms of a lateral offset of adjacent patterned layers in a plane perpendicular to the z-axis, such that the lateral offset causes a Moiré pattern. The lateral offset is chosen such that the generated Moiré pattern is spectrally equivalent, over the wavelength range $[\lambda_{min},\lambda_{max}]$, to the optical spectrum $w(\lambda)$ of the ICE associated with the characteristic to be measured.

A Moiré pattern is a superimposed pattern $M(P_1, P_2, \ldots; \delta_{1,2}, \ldots)$ created, for example, when two or more identical (or nearly identical) patterns $P_1, P_2, \ldots$ on a layer are overlaid while translated a small offset ($\delta x_{1,2}$; and/or $\delta y_{1,2}$) or rotated a small offset ($\delta \theta_{1,2}$) from one another. Features of the Moiré pattern tend to be larger than the features of the overlaid and displaced patterns $P_1, P_2, \ldots$.

A superimposition of two almost similar, sinusoidally varying, transmissive patterns $P_1$ and $P_2$ represents an example of a Moiré pattern as explained below. The first pattern $P_1$ is printed first on a transparent substrate, and the second pattern $P_2$ can be printed second over the first pattern $P_1$, keeping their coordinate axes in register. A transmission of the first pattern $P_1$ varies along the x-axis, for instance, in the following manner:

$$T_1 = \frac{1 + \sin(k_1 x)}{2}, \quad (1)$$

where $T_1=1$ represents 100% transmission through the pattern $P_1$, $T_1=0$ represents no transmission through the pattern $P_1$, and $0<T_1<1$ represents finite transmission through the pattern $P_1$. The quantity $k_1$ represents a periodic variation (also known as spatial frequency) of the pattern $P_1$'s transmission. A transmission of a similar (or almost similar) second pattern $P_2$ varies along the x-axis in a similar manner:

$$T_2 = \frac{1 + \sin(k_2 x)}{2}, \quad (2)$$

where $k_2 \approx k_1$. For example, the spatial frequencies $k_1$ and $k_2$ of the superimposed patterns $P_1$ and $P_2$ can be different from each other by 0.1%, 1% or 10%. The Moiré pattern resulting from the superimposition of the patterns $P_1$ and $P_2$ is the transmission of the Moiré pattern:

$$T_M = \frac{T_1 + T_2}{2} \quad (3)$$
$$= \frac{1 + \sin(Ax)\cos(Bx)}{2},$$
$$A = \frac{k_1 + k_2}{2}, \quad (4)$$
$$B = \frac{k_1 - k_2}{2}. \quad (5)$$

Equation (3) indicates that the Moiré pattern's transmission $T_M$ varies slowly, in accordance with an envelope $\cos(Bx)$. The Moiré pattern's spatial frequency B—equal to half of the difference of the spatial frequencies $k_1$ and $k_2$ of the superimposed patterns $P_1$ and $P_2$—is indicative the Moiré pattern having larger spatial features than the spatial features of the patterns $P_1$ and $P_2$.

Moreover, superimposition of two transmissive patterns $P_1$ and $P_2$ with the same step a that are rotated relative to each other by an angle θ represents another example of a Moiré pattern, as explained below. The first pattern $P_1$ is printed first on a transparent substrate, and the second pattern $P_2$ can be printed second over the first pattern $P_1$, keeping their coordinate axes in register. A transmission of the first pattern $P_1$ printed first on the transparent substrate varies such that a distance (e.g., along the x-axis) between clear lines (with 100% transmission) or dark lines with (with no transmission) is σ. If the second pattern $P_2$ were printed on a transparent substrate, transmission of the second pattern $P_2$ would also vary such that a distance between clear lines (with 100% transmission) or dark lines with (with no transmission) is σ. However, when the second pattern $P_2$ is printed on the first pattern $P_1$ such that lines of the second pattern $P_2$ form an angle θ relative to lines of the first pattern $P_1$, the resulting Moiré pattern has its own clear lines (passing through the intersection of the clear lines of the patterns $P_1$ and $P_2$) that make an angle of θ/2 with a normal of the lines of each of the patterns $P_1$ and $P_2$. Additionally, a distance S between the clear lines of the resulting Moiré pattern is $$S = \frac{\frac{\sigma}{2}}{\sin\left(\frac{\theta}{2}\right)}. \quad (6)$$

If the relative angular displacement θ between the patterns $P_1$ and $P_2$ is small (θ<30°), then S≈σ/θ. As such, the smaller the relative angular displacement θ, the more separation exists between the clear lines of the Moiré pattern. Once again, features of the Moiré pattern, e.g., the separation S between its clear lines, are larger than features of the superimposed patterns $P_1$ and $P_2$, e.g., the separation σ between their clear lines.

Arrangements of the multiple frequency selective surfaces of an ICE that result in various Moiré patterns are described below.

Figure 2A:
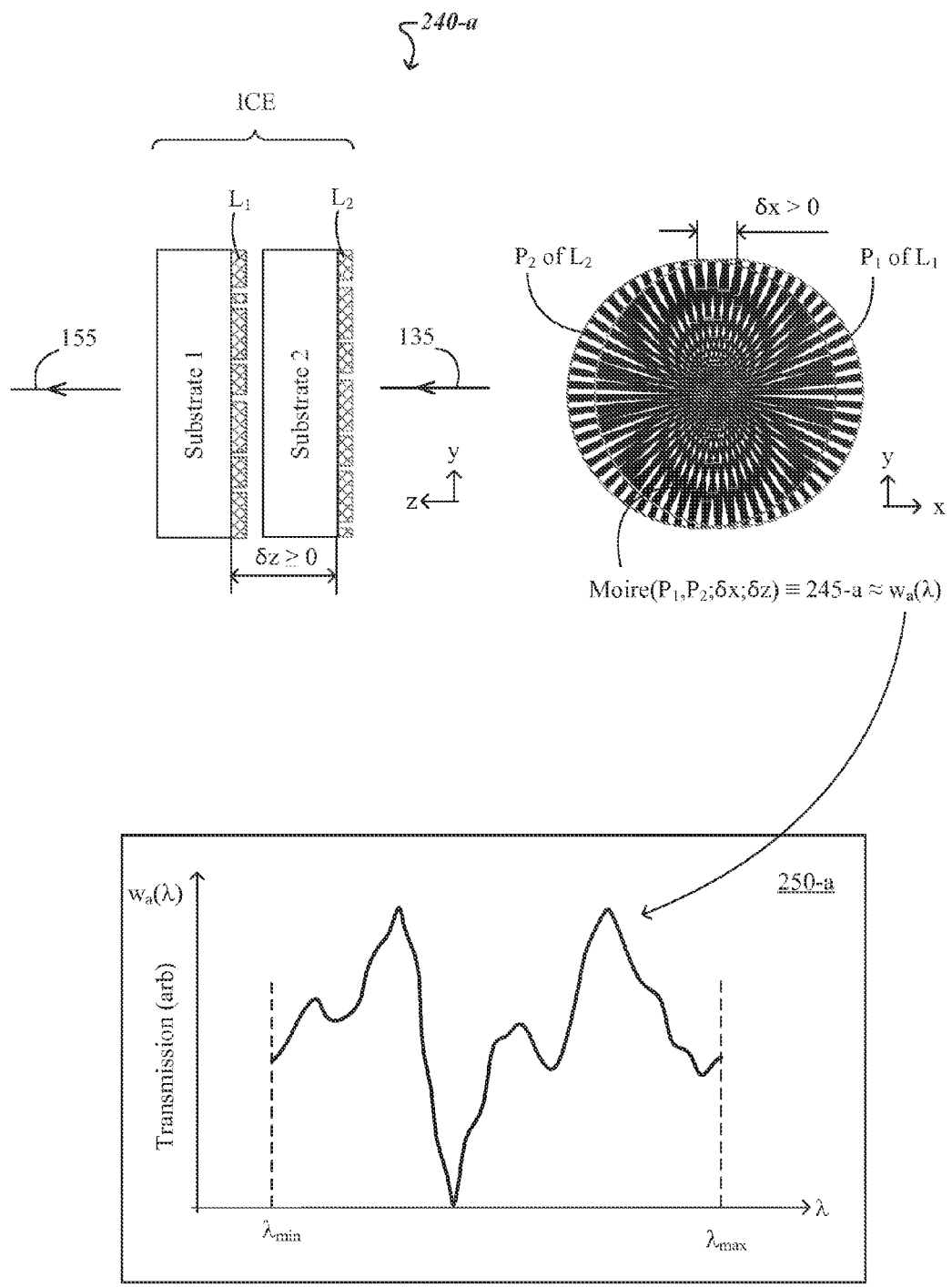
FIGS. 2A-2C show aspects of an ICE that contains multiple frequency selective surfaces displaced parallel relative to each other to form a Moiré pattern.

FIG. 2A shows an example of an ICE 240-*a* that contains multiple frequency selective surfaces. Here, the ICE 240-*a* includes two frequency selective surfaces formed respectively from a first electrically conductive layer $L_1$ patterned on a first substrate and a second electrically conductive layer $L_2$ patterned on a second substrate. In some implementations, a first pattern $P_1$ of the first layer $L_1$ is printed on the first substrate using electrically conductive inks, as described below in connection with FIG. 4. The second pattern $P_2$ of the second layer $L_2$ is printed on the second substrate in a similar manner.

In some cases, the patterns $P_1$ and $P_2$ are identical within manufacturing tolerances. In other cases the patterns $P_1$ and $P_2$ are different, such that the difference between the patterns is at most a maximum difference. The maximum difference can be quantified in terms of differences in spatial frequencies of the patterns. For example, the maximum difference between a first spatial frequency $k_1$ of the first pattern $P_1$ and a second spatial frequency $k_2$ of the second pattern $P_2$ is 0.1%, 1% or 10%. In the example illustrated in FIG. 2A, features of the patterns $P_1$ and $P_2$ are rays of finite length and width placed radially in wheel-spoke fashion. Other shapes of the features, e.g., disks, polygons, fractals, etc., and other placements of the features with respect to each other are possible.

Further in this example, the frequency selective surfaces corresponding to the first and second layers $L_1$ and $L_2$ are spaced apart from each other by an axial offset δz. In some implementations, the axial offset δz is substantially equal to a thickness $t_{S2}$ of the second substrate. By printing the electrically conductive layer $L_2$ on film sheet, for instance, the thickness of the second substrate can be selected to be as close to zero as structurally feasible, $t_{S2} \rightarrow 0$. In other implementations, the first and second substrates can be further separated from each other through spacer elements of thickness $t_{SP}$. In such case, the axial offset δz is substantially equal to the sum of the thicknesses of the second substrate and spacer elements $t_{S2}+t_{SP}$.

Furthermore in this example, the frequency selective surfaces corresponding to the first and second patterned layers $L_1$ and $L_2$ are displaced with respect to each other in a lateral direction (e.g., translated along the x-axis) by a finite (non-zero) relative offset δx>0. Other in-plane translational offsets are possible, e.g., along the y-axis, or along an arbitrary in-plane direction with finite components along both the x-axis and the y-axis. The in-plane offset δx>0 of the patterns $P_1$ and $P_2$ can be accomplished by translating the second substrate supporting the second patterned layer $L_2$ by the offset δx relative to the first substrate supporting the first patterned layer $L_1$.

An arrangement 245-a of the two frequency selective surfaces of the ICE 240-a—which is defined in FIG. 2A as (i) the patterns $P_1$ and $P_2$ respectively corresponding to the two frequency selective surfaces, (ii) the in-plane offset δx of the patterns $P_1$ and $P_2$, and (iii) the axial offset δz of the patterns $P_1$ and $P_2$—causes a Moiré pattern $M(P_1, P_2; δx; δz)$ associated with the ICE 240-a. Moreover, parameters (i), (ii) and (iii) which define the arrangement 245-a are specified such that the Moiré pattern $M(P_1, P_2; δx; δz)$ determined by the specified parameters is spectrally equivalent, over the wavelength range $[\lambda_{min}, \lambda_{max}]$, to an optical spectrum $w_a(\lambda)$ 250-a. As described above in connection with FIG. 1, the optical spectrum $w_a(\lambda)$ 250-a is associated with a characteristic to be measured. For example, if here the characteristic—to which the optical spectrum $w_a(\lambda)$ 250-a is associated—is gas-to-oil ratio (GOR), then the ICE 240-a having the arrangement 245-a of the two frequency selective surfaces can be used as part of the optical analysis tool 110 to determine GOR of wellbore fluids 130.

Note that if the in-plane offset δx of the patterns $P_1$ and $P_2$ is modified—e.g., by translating during operation of the ICE 240-a the first and second substrates supporting the respective first and second patterned layers $L_1$, $L_2$ relative to each other by an in-plane offset δx'—then a different Moiré pattern $M'(P_1, P_2; δx'; δz)$ is generated. The in-plane offset δx' can be specified such that the different Moiré pattern $M'(P_1, P_2; δx'; δz)$ is spectrally equivalent, over the wavelength range $[\lambda_{min}, \lambda_{max}]$, to another optical spectrum $w_a'(\lambda)$ 250-a' (not shown in FIG. 2A) associated with another characteristic to be measured. For example, if here the other characteristic—to which the optical spectrum $w'_a(\lambda)$ 250-a' is associated—is density, then the ICE 240-a having the other arrangement of the two frequency selective surfaces can be used as part of the optical analysis tool 110 to determine density of wellbore fluids 130. In this manner, multiple optical spectra associated with multiple characteristics to be measured are available for weighting the sample modified light 135 that illuminates the ICE 240-a, during operation thereof.

In other implementations, not illustrated in FIG. 2A, the axial offset δz of the frequency selective surfaces corresponding to the first and second patterned layers $L_1$ and $L_2$ is zero. In this case, the second layer $L_2$ is patterned directly onto the first patterned layer $L_1$, such that the second pattern $P_2'$ is laterally offset relative to the first pattern $P_1'$ by δx', as described below in connection with FIG. 4. The resulting Moiré pattern $M(P_1', P_2'; δx'; δz=0)$ causes that the ICE 240-a have an optical spectrum $w_a(\lambda)$ 250-a'' (not shown in FIG. 2A). Once again, through appropriate specification of the parameters which define this arrangement 245-a'', a Moiré pattern $M(P_1', P_2'; δx'; δz=0)$ can be generated to be spectrally equivalent, over the wavelength range $[\lambda_{min}, \lambda_{max}]$, to the optical spectrum $w_a(\lambda)$ 250-a'' associated with a given characteristic to be measured. Note that in the latter implementations, when the second layer $L_2$ is patterned directly onto the previously patterned layer $L_1$, the obtained Moiré pattern $M(P_1', P_2'; δx'; δz=0)$ is frozen into the ICE 240-a. As such, a single optical spectrum $w_a(\lambda)$ 250-a'' associated with the given characteristic to be measured is available for weighting the sample modified light 135 incident onto the ICE 240-a, during operation thereof.

Figure 2B:
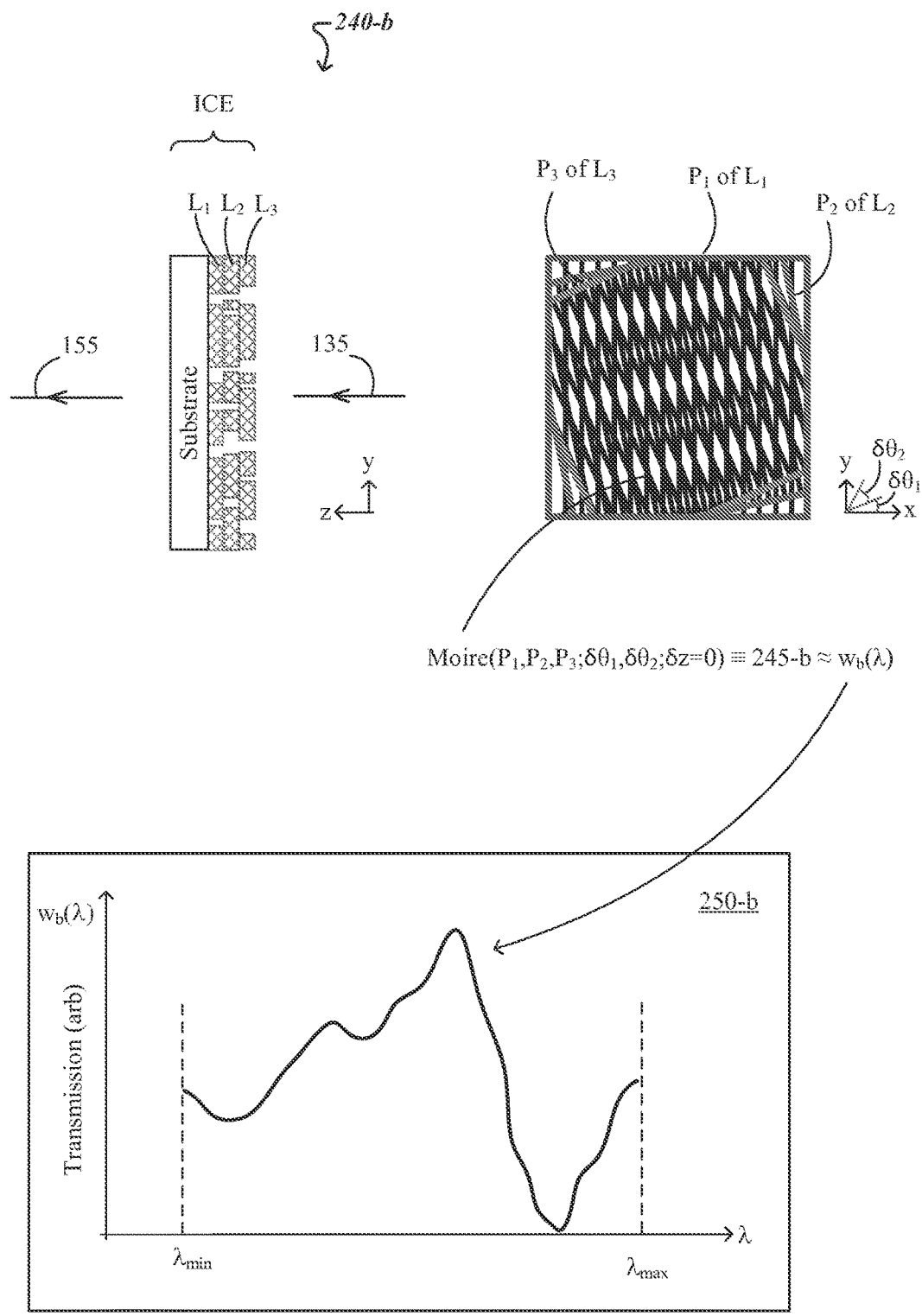

FIG. 2B shows another example of an ICE 240-b that contains multiple frequency selective surfaces. Here, the ICE 240-b includes three frequency selective surfaces formed respectively from a first electrically conductive layer $L_1$ patterned on a substrate, a second electrically conductive layer $L_2$ patterned on the first electrically conductive layer $L_1$, and a third electrically conductive layer $L_3$ patterned on the second electrically conductive layer $L_2$. In some implementations, the first pattern $P_1$ is printed on the substrate using electrically conductive inks, as described below in connection with FIG. 4. The second and third patterns $P_2$, $P_3$ are printed on respective previously printed pattern $P_1$, $P_2$ in a similar manner.

In some cases, the patterns $P_1$, $P_2$ and $P_3$ are identical within manufacturing tolerances. In other cases the patterns $P_1$, $P_2$ and $P_3$ are different, such that the differences between the patterns are at most a maximum difference. The maximum difference can be quantified in terms of differences in spatial frequencies of the patterns. For example, a first spatial frequency $k_1$ of the first pattern $P_1$, a second spatial frequency $k_2$ of the second pattern $P_2$ and a third spatial frequency $k_3$ of the third pattern $P_3$ are different from each other by a maximum difference of 0.1%, 1% or 10%. In the example illustrated in FIG. 2B, features of the patterns $P_1$, $P_2$ and $P_3$ are parallel lines of finite width separated by a given separation. Other shapes of the features, e.g., disks, triangles, hexagons, fractals, etc., and other placements of the features with respect to each other are possible.

Further in this example, the frequency selective surfaces corresponding to the first and second patterned layers $L_1$ and $L_2$ are displaced with respect to each other in a lateral direction (e.g., rotated around the z-axis) by a finite (non-zero) relative angular offset $δθ_1>0$, and the frequency selective surfaces corresponding to the second and third patterned layers $L_2$ and $L_3$ are displaced with respect to each other in the same lateral direction (e.g., rotated around the z-axis) by another finite (non-zero) relative angular offset $δθ_2>0$. In some implementations, the frequency selective surfaces corresponding to the first, second and third patterned layers $L_1$, $L_2$ and $L_3$ are rotated with respect to each other (e.g., rotated around the z-axis) by the same finite (non-zero) relative angular offset $δθ_1=δθ_2>0$. In the example illustrated in FIG. 2B, $δθ_1=δθ_2=12°$. The first in-plane offset $δθ_2>0$ of the patterns $P_1$ and $P_2$ can be accomplished by rotating the substrate supporting the first patterned layer $L_1$ by the first offset 608 relative to a reference coordinate system prior to patterning the second electrically conductive layer $L_2$ onto the first patterned layer $L_1$. Similarly, the second in-plane offset $δθ_2>0$ of the patterns $P_2$ and $P_3$ can be accomplished by rotating the substrate supporting the first patterned layer $L_1$ and the second patterned layer $L_2$ by the second offset $δθ_2$ relative to the second pattern $P_2$ (or by a cumulative offset $δθ_1+δθ_2$ relative to the reference coordinate system) prior to patterning the third electrically conductive layer $L_3$ onto the second patterned layer $L_2$.

An arrangement 245-b of the three frequency selective surfaces of the ICE 240-b—which is defined in FIG. 2B as (i) the patterns $P_1$, $P_2$ and $P_3$ respectively corresponding to the three frequency selective surfaces, and (ii) the in-plane offset $δθ_1$ of the patterns $P_1$ and $P_2$, and the in-plane offset $δθ_2$ of the patterns $P_2$ and $P_3$—causes a Moiré pattern $M(P_1, P_2, P_3; δθ_1, δθ_2)$ associated with the ICE 240-b. Moreover, parameters (i) and (ii) which define the arrangement 245-b are specified such that the Moiré pattern $M(P_1, P_2, P_3; δθ_1, δθ_2)$ determined by the specified parameters is spectrally equivalent, over the wavelength range $[\lambda_{min},\lambda_{max}]$, to an optical spectrum $w_b(\lambda)$ 250-$b$. As described above in connection with FIG. 1, the optical spectrum $w_b(\lambda)$ 250-$b$ is associated with a characteristic to be measured. For example, if here the characteristic—to which the optical spectrum $w_b(\lambda)$ 250-$b$ is associated—is pH, then the ICE 240-$b$ having the arrangement 245-$b$ of the three frequency selective surfaces can be used as part of the optical analysis tool 110 to determine pH of wellbore fluids 130.

Note that because the second and third layers $L_2$, $L_3$ are patterned directly onto the respective previously patterned layer $L_1$, $L_2$, the obtained Moiré pattern M($P_1$, $P_2$, $P_3$; $\delta\theta_1$, $\delta\theta_2$) is frozen into the ICE 240-$b$. As such, a single optical spectrum $w_b(\lambda)$ 250-$a$ associated with the particular characteristic to be measured is available for weighting the sample modified light 135 incident onto the ICE 240-$b$, during operation thereof.

Another ICE than contains multiple frequency selective surfaces is described below, such that the ICE accommodates, during operation thereof, different arrangements of the frequency selective surfaces, each of the different arrangements causing an associated Moiré pattern that is spectrally equivalent, over an associated wavelength range, to an associated optical spectrum, such that the combined optical spectra are associated with a characteristic to be measured.

Figure 2C:
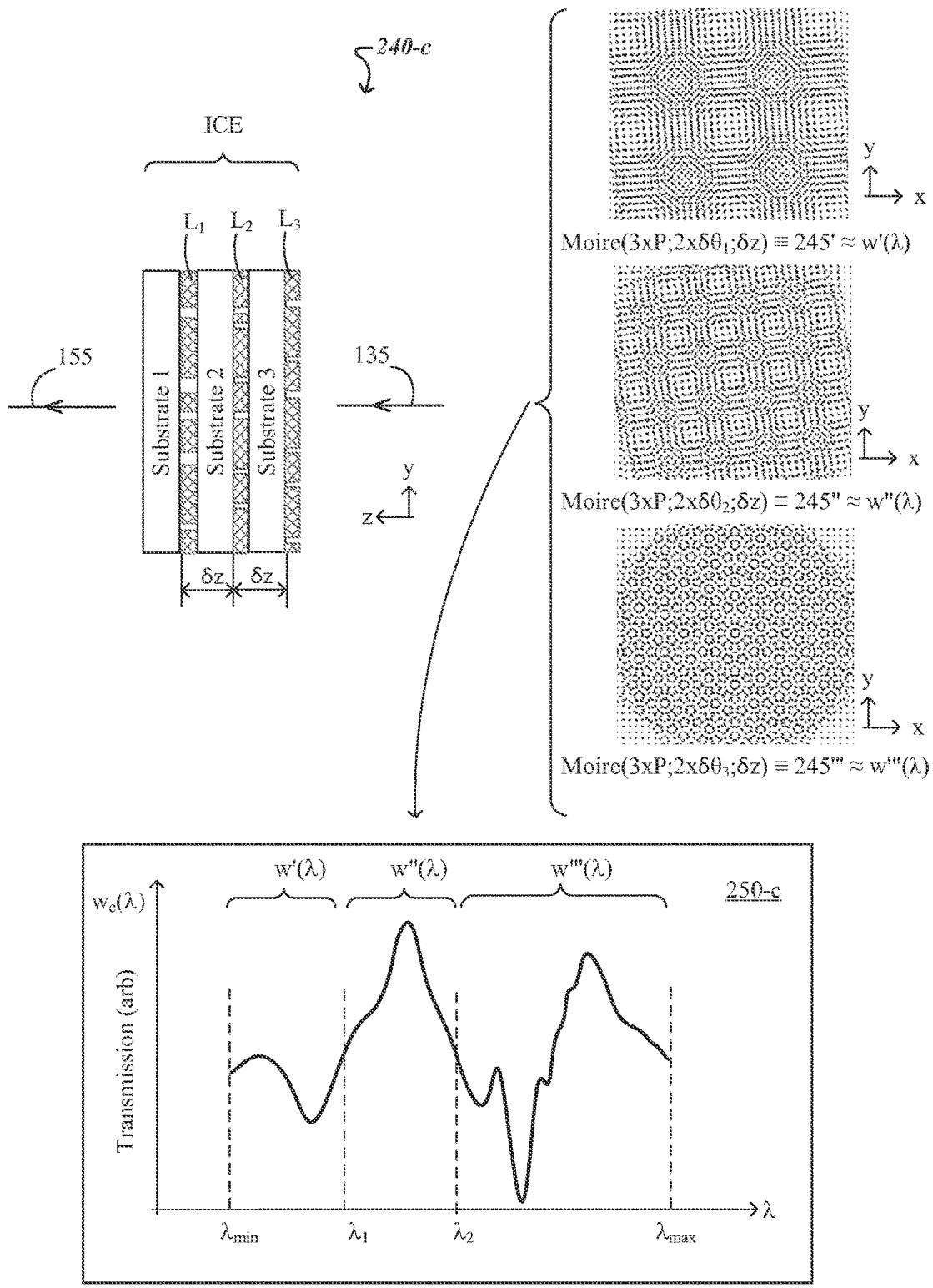

FIG. 2C shows another example of an ICE 240-$c$ that contains multiple frequency selective surfaces. Here, the ICE 240-$c$ includes three frequency selective surfaces formed respectively from a first electrically conductive layer $L_1$ patterned on a first substrate, a second electrically conductive layer $L_2$ patterned on a second substrate and a third electrically conductive layer $L_3$ patterned on a third substrate. In some implementations, a first pattern $P_1$ of the first layer $L_1$ is printed on the first substrate using electrically conductive inks, as described below in connection with FIG. 4. The second pattern $P_2$ of the second layer $L_2$ and the third pattern $P_3$ of the third layer $L_3$ are printed on the second substrate and third substrate, respectively, in a manner similar to the printing of the first layer $L_1$.

In the example illustrated in FIG. 2B, the patterns $P_1$, $P_2$ and $P_3$ are identical (within manufacturing tolerances) and are referred to as a pattern P of the frequency selective surfaces. Here, features of the pattern P are dots of finite area placed at vertices of a periodic lattice with rectangular unit cell. Other shapes of the features, e.g., disks, triangles, hexagons, fractals, etc., and other placements of the features with respect to each other are possible.

Further in this example, the frequency selective surfaces corresponding to the first, second and third layers $L_1$, $L_2$, $L_3$ are spaced apart from each other by the same axial offset $\delta z$. In the example illustrated in FIG. 2C, the axial offset $\delta z$ between each of adjacent layers $L_1$ and $L_2$ or $L_2$ and $L_3$ is substantially equal to a thickness $t_{S2}=t_{S3}=t$ of each of the second and third substrates. By printing the electrically conductive layers $L_2$ and $L_3$ on respective film sheets, for instance, the thickness of each of the second and third substrates can be selected to be as close to zero as structurally feasible, $t \to 0$. In other implementations (not shown in FIG. 2C), the first and second substrates and/or the second and third substrates can be further separated from each other through spacer elements of thickness $t_{SP}$. In such case, the axial offset $\delta z$ is substantially equal to the sum of the thicknesses of each of the second and third substrates and spacer elements $t+t_{SP}$.

Furthermore in this example, the frequency selective surfaces corresponding to the first, second and third patterned layers $L_1$, $L_2$ and $L_3$ are rotated with respect to each other (e.g., rotated around the z-axis) by the same finite (non-zero) relative angular offset $\delta\theta > 0$. The in-plane offset $\delta\theta > 0$ of the patterned layers $L_1$ and $L_2$ can be accomplished by rotating the second substrate supporting the second patterned layer $L_2$ by the offset $\delta\theta$ relative to the first substrate supporting the first patterned layer $L_1$. Similarly, the in-plane offset $\delta\theta > 0$ of the patterned layers $L_2$ and $L_3$ can be accomplished by rotating the substrate supporting the third patterned layer $L_3$ by the offset $\delta\theta$ relative to the second substrate supporting the second patterned layer $L_2$.

A first arrangement 245' of the three frequency selective surfaces of the ICE 240-$c$—which is defined in FIG. 2C as (i) the pattern P corresponding to each of the three frequency selective surfaces, (ii) the axial offset $\delta z$ between each of the adjacent patterned layers $L_1$, $L_2$ and $L_2$, $L_3$, and (iii) a first in-plane offset $\delta\theta_1$ between each of the adjacent patterned layers $L_1$, $L_2$ and $L_2$, $L_3$—causes a first Moiré pattern M'(P; $\delta\theta_1$; $\delta z$) associated with the ICE 240-$c$. In the example illustrated in FIG. 2C, $\delta\theta_1=4°$. Here, parameters (i), (ii) and (iii) which define the first arrangement 245' are specified such that the first Moiré pattern M'(P; $\delta\theta_1$; $\delta z$) determined by the specified parameters is spectrally equivalent, over a first sub-range $[\lambda_{min},\lambda_1]$ of the wavelength range $[\lambda_{min},\lambda_{max}]$, to a first spectral portion w'($\lambda$) of an optical spectrum $w_c(\lambda)$ 250-$c$ illustrated in FIG. 2C.

A second arrangement 245" of the three frequency selective surfaces of the ICE 240-$c$—which is defined in FIG. 2C as (i) the pattern P corresponding to each of the three frequency selective surfaces, (ii) the axial offset $\delta z$ between each of the adjacent patterned layers $L_1$, $L_2$ and $L_2$, $L_3$, and (iii) a second in-plane offset $\delta\theta_1$ between each of the adjacent patterned layers $L_1$, $L_2$ and $L_2$, $L_3$—causes a second Moiré pattern M"(P; $\delta\theta_2$; $\delta z$) associated with the ICE 240-$c$. In the example illustrated in FIG. 2C, $\delta\theta_2=16°$. Here, parameters (i), (ii) and (iii) which define the second arrangement 245" are specified such that the second Moiré pattern M"(P; $\delta\theta_2$; $\delta z$) determined by the specified parameters is spectrally equivalent, over a second sub-range $[\lambda_1,\lambda_2]$ of the wavelength range $[\lambda_{min},\lambda_{max}]$, to a second spectral portion w"($\lambda$) of the optical spectrum $w_c(\lambda)$ 250-$c$.

A third arrangement 245''' of the three frequency selective surfaces of the ICE 240-$c$—which is defined in FIG. 2C as (i) the pattern P corresponding to each of the three frequency selective surfaces, (ii) the axial offset $\delta z$ between each of the adjacent patterned layers $L_1$, $L_2$ and $L_2$, $L_3$, and (iii) a third in-plane offset $\delta\theta_3$ between each of the adjacent patterned layers $L_1$, $L_2$ and $L_2$, $L_3$—causes a third Moiré pattern M'''(P; $\delta\theta_3$; $\delta z$) associated with the ICE 240-$c$. In the example illustrated in FIG. 2C, $\delta\theta_3=60°$. Here, parameters (i), (ii) and (iii) which define the third arrangement 245''' are specified such that the third Moiré pattern M'''(P; $\delta\theta_3$; $\delta z$) determined by the specified parameters is spectrally equivalent, over a third sub-range $[\lambda_2,\lambda_{max}]$ of the wavelength range $[\lambda_{min},\lambda_{max}]$, to a third spectral portion w'''($\lambda$) of the optical spectrum $w_c(\lambda)$ 250-$c$.

In general, $K \geq 2$ different arrangements of the three frequency selective surfaces of the ICE 240-$c$ can cause K different Moiré patterns $M_j$(P; $\delta\theta_j$; $\delta z$), where $j=1, \ldots, K$, such that each of the Moiré patterns $M_j$(P; $\delta\theta_j$; $\delta z$) is spectrally equivalent to a corresponding $j^{th}$ sub-range $[\lambda_j, \lambda_{j+1}]$ of the wavelength range $[\lambda_{min},\lambda_{max}]$. In this manner, by adjusting the relative orientation $\delta\theta_j$ between adjacent layers $L_j$, $L_{j+1}$, the entire optical spectrum $w_c(\lambda)$ 250-$c$ can be precisely matched.

As described above in connection with FIG. 1, the optical spectrum $w_c(\lambda)$ 250-$c$ over the entire wavelength range $[\lambda_{min},\lambda_{max}]$ is associated with a characteristic to be measured. For example, if here the characteristic—to which the optical spectrum w(λ) 250-*c* is associated—is viscosity, then the ICE 240-*c* having the combined arrangements {245', 245" and 245'''} of the three frequency selective surfaces can be used as part of the optical analysis tool 110 to determine viscosity of wellbore fluids 130. In some implementations, the ICE 240-*c* described above can sequentially have different arrangements of its three frequency selective surfaces, and hence, it is operated in the following manner while measuring the characteristic (e.g., viscosity) of the sample.

Adjacent substrates of the ICE 240-*c* are rotated with respect to each other by the first in-plane offset $\delta\theta_1$ to generate the first Moiré pattern M'(P; $\delta\theta_1$; $\delta z$) that is spectrally equivalent to the first spectral portion w'(λ). The first in-plane offset 608 can be a default relative rotation between the frequency selective surfaces of the ICE 240-*c*. While the frequency selective surfaces are arranged under the first arrangement 245' that causes the first Moiré pattern M'(P; $\delta\theta_1$; $\delta z$), the ICE 240-*c* is illuminated by the sample modified light 135 for a first time interval $\delta T_1$. A first filter that limits a spectrum of the sample modified light 135 to the first spectral portion $[\lambda_{min},\lambda_1]$ can be used in conjunction with the first arrangement 245'. A spectrum of a first instance of the processed light 155 represents a spectrum of the sample modified light 135 weighted, over the first spectral portion $[\lambda_{min},\lambda_1]$, by the ICE 240-*c* in accordance with the first spectral portion w'(λ). A first instance of the detector signal 165'—which is generated by integration of the processed light 155 over the first spectral portion $[\lambda_{min},\lambda_1]$ for the first time interval $\delta T_1$—is recorded at this time.

Further, the adjacent substrates of the ICE 240-*c* are rotated with respect to each other by the second in-plane offset $\delta\theta_2$ to generate the second Moiré pattern M"(P; $\delta\theta_2$; $\delta z$) that is spectrally equivalent to the second spectral portion w"(λ). In some implementations, the relative rotation by the second in-plane offset $\delta\theta_2$ between the frequency selective surfaces of the ICE 240-*c* can be performed automatically, in a pre-programmed manner, using rotating actuators associated with the ICE 240-*c*. While the frequency selective surfaces are arranged under the second arrangement 245" that causes the second Moiré pattern M"(P; $\delta\theta_2$; $\delta z$), the ICE 240-*c* is illuminated by the sample modified light 135 for a second time interval $\delta T_2$. A second filter that limits the spectrum of the sample modified light 135 to the second spectral portion $[\lambda_1,\lambda_2]$ can be used in conjunction with the second arrangement 245". A spectrum of a second instance of the processed light 155 represents the spectrum of the sample modified light 135 weighted, over the second spectral portion $[\lambda_1,\lambda_2]$, by the ICE 240-*c* in accordance with the second spectral portion w"(λ). A second instance of the detector signal 165"—which is generated by integration of the processed light 155 over the second spectral portion $[\lambda_1,\lambda_2]$ for the second time interval $\delta T_2$—is recorded at this time.

Furthermore, the adjacent substrates of the ICE 240-*c* are rotated with respect to each other by the third in-plane offset $\delta\theta_3$ to generate the third Moiré pattern M'''(P; $\delta\theta_3$; $\delta z$) that is spectrally equivalent to the third spectral portion w'''(λ). In some implementations, the relative rotation by the third in-plane offset $\delta\theta_3$ between the frequency selective surfaces of the ICE 240-*c* can be performed automatically, in a pre-programmed manner, using the rotating actuators associated with the ICE 240-*c*. While the frequency selective surfaces are arranged under the third arrangement 245''' that causes the third Moiré pattern M'''(P; $\delta\theta_3$; $\delta z$), the ICE 240-*c* is illuminated by the sample modified light 135 for a first time interval $\delta T_3$. A third filter that limits the spectrum of the sample modified light 135 to the third spectral portion $[\lambda_2,\lambda_{max}]$ can be used in conjunction with the third arrangement 245'''. A spectrum of a third instance of the processed light 155 represents the spectrum of the sample modified light 135 weighted, over the third spectral portion $[\lambda_2,\lambda_{max}]$, by the ICE 240-*c* in accordance with the third spectral portion w'''(λ). A third instance of the detector signal 165'''—which is generated by integration of the processed light 155 over the third spectral portion $[_2,\lambda_{max}]$ for the third time interval $\delta T_3$—is recorded at this time.

A value of the characteristic (e.g., viscosity) of the sample—corresponding to the spectrum of the sample modified light 135 weighted by the optical spectrum $w_c(\lambda)$ 250-*c* over the entire wavelength range $[\lambda_{min},\lambda_{max}]$—is proportional to a combination of the first, second and third instances of the detector signal 165', 165" and 165''' generated for the respective first 245', second 245" and third 245''' arrangements of the frequency selective surfaces of the ICE 240-*c*. For example, the combination can be a weighted sum of the first, second and third recorded instances of the detector signals 165', 165" and 165'''. The weights of the first, second and third recorded instances of the detector signal can be proportional to the respective integration times, $\delta T_1$, $\delta T_2$ and $\delta T_3$, for instance.

In other implementations not illustrated in FIG. 2C, the three frequency selective surfaces of the ICE 240-*c* are formed using only the first substrate, in the following manner. The first electrically conductive layer $L_1$ is patterned with the pattern P over a first portion of the first substrate, over a second portion of the first substrate adjacent the first portion of the first substrate, and over a third portion of the first substrate adjacent the first and second portions of the first substrate. In some implementations, the first, second and third portions of the first substrate can have substantially the same area.

Over the first portion of the first substrate, the second electrically conductive layer $L_2$ is patterned directly onto the first patterned layer $L_1$ with the same pattern P rotated relative to the first patterned layer $L_1$ by the first in-plane offset $\delta\theta_1$, and the third electrically conductive layer $L_3$ is patterned directly onto the second patterned layer $L_2$ with the same pattern P rotated relative to the second patterned layer $L_2$ by the first in-plane offset 61. As such, an arrangement 245' of the first $L_1$, second $L_2$ and third $L_3$ patterned layers causes, over the first portion of the first substrate, a first Moiré pattern M'(P; $\delta\theta_1$; $\delta z$=0) that is spectrally equivalent, over a first sub-range $[\lambda_{min},\lambda_1]$ of the wavelength range $[\lambda_{min},\lambda_{max}]$, to a first spectral portion w'(λ) of the optical spectrum $w_c(\lambda)$ 250-*c*.

Further, over the second portion of the substrate, the second electrically conductive layer $L_2$ is patterned directly onto the first patterned layer $L_1$ with the same pattern P rotated relative to the first patterned layer $L_1$ by the second in-plane offset $\delta\theta_2$, and the third electrically conductive layer $L_3$ is patterned directly onto the second patterned layer $L_2$ with the same pattern P rotated relative to the second patterned layer $L_2$ by the second in-plane offset $\delta\theta_2$. As such, an arrangement 245" of the first $L_1$, second $L_2$ and third $L_3$ patterned layers causes, over the second portion of the first substrate, a second Moiré pattern M"(P; $\delta\theta_2$; $\delta z$=0) that is spectrally equivalent, over a second sub-range $[\lambda_1,\lambda_2]$ of the wavelength range $[\lambda_{min},\lambda_{max}]$, to a second spectral portion w"(λ) of the optical spectrum $w_c(\lambda)$ 250-*c*.

Furthermore, over the third portion of the substrate, the second electrically conductive layer $L_2$ is patterned directly onto the first patterned layer $L_1$ with the same pattern P rotated relative to the first patterned layer $L_1$ by the third in-plane offset $\delta\theta_3$, and the third electrically conductive layer $L_3$ is patterned directly onto the second patterned layer $L_2$ with the same pattern P rotated relative to the second patterned layer $L_2$ by the third in-plane offset $\delta\theta_3$. As such, an arrangement 245''' of the first $L_1$, second $L_2$ and third $L_3$ patterned layers causes, over the third portion of the first substrate, a third Moiré pattern M'''(P; $\delta\theta_3$; $\delta z$=0) that is spectrally equivalent, over a third sub-range $[\lambda_2,\lambda_{max}]$ of the wavelength range $[\lambda_{min},\lambda_{max}]$, to a third spectral portion w'''($\lambda$) of the optical spectrum $w_c(\lambda)$ 250-c.

In some implementations, the different arrangements of portions of the three frequency selective surfaces of the ICE 240-c can be sequentially illuminated by the sample modified light 135, and hence, the ICE 240-c is operated in the following manner during the measurement of the third characteristic of the sample.

For instance, the ICE 240-c is illuminated for a first time interval $\delta T_1$ by the sample modified light 135 over the first portion of the first substrate corresponding to the first arrangement 245' of the frequency selective surfaces that causes the first Moiré M'(P; $\delta\theta_1$; $\delta z$=0) that is spectrally equivalent to the first spectral portion w'($\lambda$). A first filter that limits a spectrum of the sample modified light 135 to the first spectral portion $[\lambda_{min},\lambda_1]$ can be used while illuminating the first arrangement 245'. A spectrum of a first instance of the processed light 155 represents a spectrum of the sample modified light 135 weighted, over the first spectral portion $[\lambda_{min},\lambda_1]$, by the ICE 240-c in accordance with the first spectral portion w'($\lambda$). A first instance of the detector signal 165'—which is generated by integration of the processed light 155 over the first spectral portion $[\lambda_{min},\lambda_1]$ for the first time interval $\delta T_1$—is recorded at this time.

Further, the ICE 240-c is illuminated for a second time interval $\delta T_2$ by the sample modified light 135 over the second portion of the first substrate corresponding to the second arrangement 245" of the frequency selective surfaces that causes the second Moiré M"(P; $\delta\theta_2$; $\delta z$=0) that is spectrally equivalent to the second spectral portion w"($\lambda$). In some implementations, the sample modified light 135 is automatically redirected from previously illuminating the first portion of the first substrate to currently illuminating the second portion of the first substrate, in a pre-programmed manner, using scanning optics associated with the ICE 240-c. A second filter that limits the spectrum of the sample modified light 135 to the second spectral portion $[\lambda_1,\lambda_2]$ can be used while illuminating the second arrangement 245". A spectrum of a second instance of the processed light 155 represents the spectrum of the sample modified light 135 weighted, over the second spectral portion $[\lambda_1,\lambda_2]$, by the ICE 240-c in accordance with the second spectral portion w"($\lambda$). A second instance of the detector signal 165"—which is generated by integration of the processed light 155 over the second spectral portion $[\lambda_1,\lambda_2]$ for the second time interval $\delta T_2$—is recorded at this time.

Furthermore, the ICE 240-c is illuminated for a third time interval $\delta T_3$ by the sample modified light 135 over the third portion of the first substrate corresponding to the third arrangement 245''' of the frequency selective surfaces that causes the third Moiré M'''(P; $\delta\theta_3$; $\delta z$=0) that is spectrally equivalent to the third spectral portion w'''($\lambda$). In some implementations, the sample modified light 135 is automatically redirected from previously illuminating the second portion of the first substrate to currently illuminating the third portion of the first substrate, in a pre-programmed manner, using scanning optics associated with the ICE 240-c. A third filter that limits the spectrum of the sample modified light 135 to the third spectral portion $[\lambda_2,\lambda_{max}]$ can be used while illuminating the third arrangement 245'''. A spectrum of a third instance of the processed light 155 represents the spectrum of the sample modified light 135 weighted, over the third spectral portion $[\lambda_2,\lambda_{max}]$, by the ICE 240-c in accordance with the third spectral portion w'''($\lambda$). A third instance of the detector signal 165'''—which is generated by integration of the processed light 155 over the third spectral portion $[\lambda_2,\lambda_{max}]$ for the third time interval $\delta T_3$—is recorded at this time.

A value of the characteristic (e.g., viscosity) of the sample—corresponding to the spectrum of the sample modified light 135 weighted by the optical spectrum $w_c(\lambda)$ 250-c over the wavelength range $[\lambda_{min},\lambda_{max}]$—is proportional to a combination of the first, second and third instances of the detector signal 165', 165" and 165''' generated when respective portions of the first substrate corresponding to the first 245', second 245" and third 245''' arrangements of the frequency selective surfaces of the ICE 240-c are illuminated. For example, the combination can be a weighted sum of the first, second and third recorded instances of the detector signals 165', 165" and 165'''. The weights of the first, second and third recorded instances of the detector signal 165', 165" and 165''' can be proportional to the respective integration times, $\delta T_1$, $\delta T_2$ and $\delta T_3$, and/or respective relative areas of the first, second and third portions of the first substrate corresponding to the first 245', second 245" and third 245''' arrangements, for instance.

In other implementations, the first, second and third portions of the first substrate corresponding to the first 245', second 245" and third 245''' arrangements of the three frequency selective surfaces of the ICE 240-c can be concurrently illuminated by the sample modified light 135, and hence, the ICE 240-c is operated in the following manner while measuring the characteristic (e.g., viscosity) of the sample.

Here, a first portion of the processed light 155 is output by the ICE 240-c from the sample modified light 135 that illuminates the first portion of the first substrate corresponding to the first arrangement 245' of the frequency selective surfaces that causes the first Moiré M'(P; $\delta\theta_1$; $\delta z$=0) that is spectrally equivalent to the first spectral portion w'($\lambda$). A spectrum of the first portion of the processed light 155 represents a spectrum of the sample modified light 135 weighted, over the first spectral portion $[\lambda_{min},\lambda_1]$, by the ICE 240-c in accordance with the first spectral portion w'($\lambda$). A second portion of the processed light 155 is output, concurrently with the first portion of the processed light 155, by the ICE 240-c from the sample modified light 135 that illuminates the second portion of the first substrate corresponding to the second arrangement 245" of the frequency selective surfaces that causes the second Moiré M"(P; $\delta\theta_2$; $\delta z$=0) that is spectrally equivalent to the second spectral portion w"($\lambda$). A spectrum of the second portion of the processed light 155 represents a spectrum of the sample modified light 135 weighted, over the second spectral portion $[\lambda_1,\lambda_2]$, by the ICE 240-c in accordance with the second spectral portion w"($\lambda$). A third portion of the processed light 155 is output, concurrently with the first and second portions of the processed light 155, by the ICE 240-c from the sample modified light 135 that illuminates the third portion of the first substrate corresponding to the third arrangement 245''' of the frequency selective surfaces that causes the third Moiré M'''(P; $\delta\theta_3$; $\delta z$=0) that is spectrally equivalent to the third spectral portion w'''($\lambda$). A spectrum of the third portion of the processed light 155 represents a spectrum of the sample modified light 135 weighted, over the second spectral portion $[\lambda_1,\lambda_2]$, by the ICE 240-c in accordance with the second spectral portion w"($\lambda$).

A value of the characteristic (e.g., viscosity) of the sample—corresponding to the spectrum of the sample modified light 135 weighted by the optical spectrum $w_c(\lambda)$ 250-c over the wavelength range $[\lambda_{min},\lambda_{max}]$—is proportional to a detector signal 165. In this case, the detector signal 165 is generated by concurrent integration of the first portion of the processed light 155 over the first spectral portion $[\lambda_{min},\lambda_1]$, the second portion of the processed light 155 over the second spectral portion $[\lambda_1,\lambda_2]$ and the third portion of the processed light 155 over the third spectral portion $[\lambda_2,\lambda_{max}]$.

Arrangements of the multiple frequency selective surfaces of an ICE were described above that result in various Moiré patterns, such that the Moiré patterns are spectrally equivalent with respective characteristics to be measured.

In other implementations, frequency selective surfaces of an ICE are respective three or more layers of electrically conductive materials patterned with corresponding patterns and stacked along the z-axis, for instance. Here, an arrangement of the three or more patterned layers with respect to each other is defined in terms of an offset of adjacent patterned layers along the z-axis, also referred to as an axial offset. The three or more patterned layers arranged in this manner form a 3D lattice of patterned layers. The 3D lattice of patterned layers has translational symmetry at least along the z-axis. Further, a magnitude of the axial offset has substantially the same order of magnitude as a scale of features of the patterns of the patterned layers. For instance, if the patterns have feature sizes of order 100 µm, then the axial offset between adjacent patterned layers also is of order 100 µm, as opposed to being of order 10 µm or 1 mm. Additionally, depending on placement of the features of the patterned layers, the 3D lattice of patterned layers can also have translational and/or rotational symmetry orthogonal to the z-axis. Moreover, parameters of the arrangement of the frequency selective surfaces including (i) patterns of the three or more patterned layers and (ii) the axial offset of adjacent patterned layers along the z-axis are specified such that the 3D lattice of patterned layers is spectrally equivalent, over the wavelength range $[\lambda_{min},\lambda_{max}]$, to the optical spectrum w($\lambda$) of the ICE associated with the characteristic to be measured.

Figure 3:
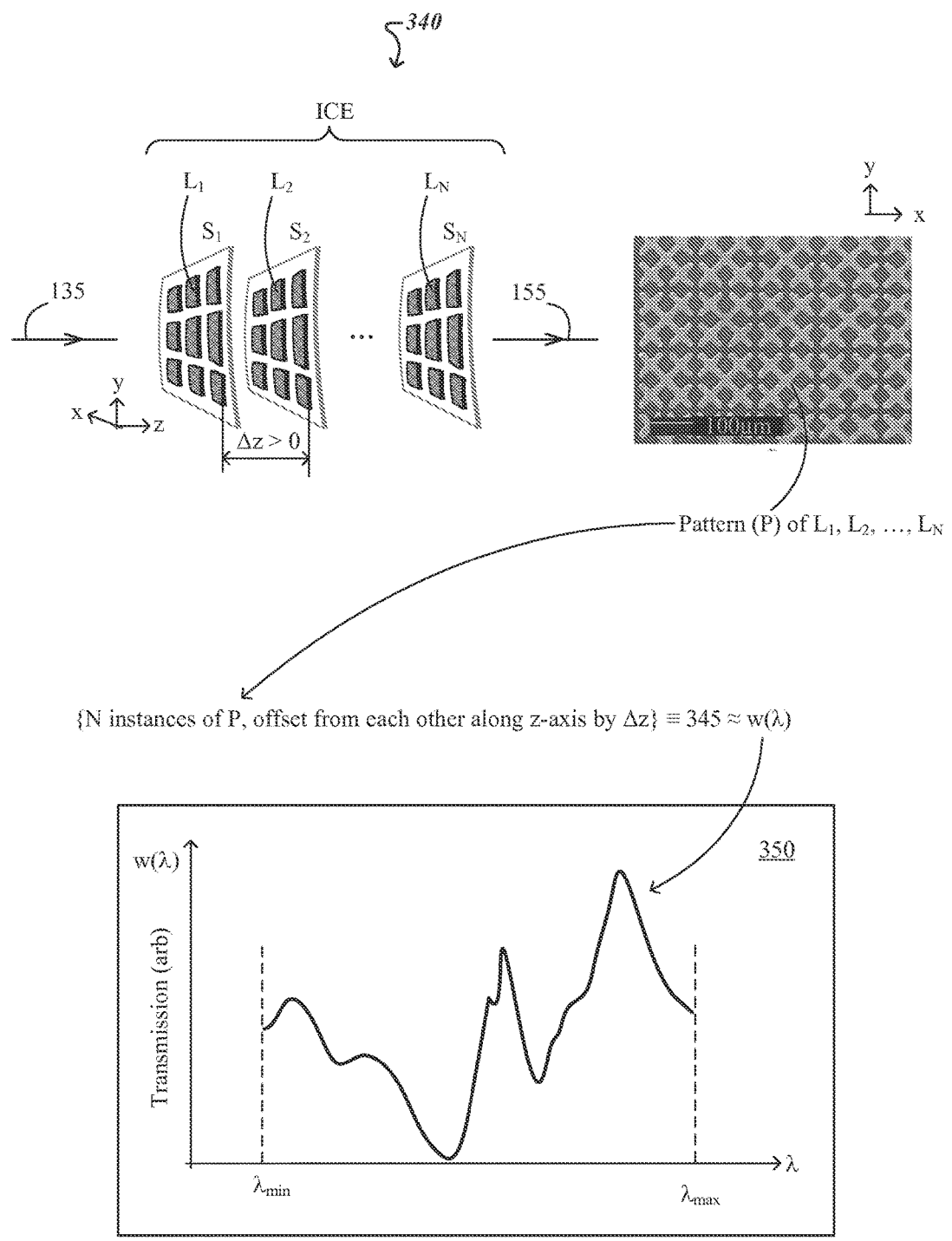
FIG. 3 shows an ICE that contains multiple frequency selective surfaces displaced orthogonal relative to each other to form a three dimensional (3D) lattice of frequency selective surfaces.

FIG. 3 shows an example of an ICE 340 that contains N frequency selective surfaces, where N≥3. Each frequency selective surface is formed from an associated electrically conductive layer $L_j$ patterned on a $j^{th}$ substrate, where j=1, . . . , N. In some implementations, a $j^{th}$ pattern $P_j$ of the $j^{th}$ layer $L_j$ is printed on the $j^{th}$ substrate using electrically conductive inks, as described below in connection with FIG. 4.

In the example illustrated in FIG. 3, the patterns $P_1$, $P_2$, . . . , $P_N$ of the respective patterned layers $L_1$, $L_2$, . . . , $L_N$ are common, the common pattern being referred to as a pattern P.

Here, features of the pattern P are fractal cross dipole patches. Moreover, the pattern P is laterally periodic along the x-axis and along the y-axis. Primary cross dipoles have arm lengths of 170 µm, and secondary cross dipoles have arm lengths of 70 µm. A line width of the primary and secondary cross dipoles is 15 µm. The spacing between the fractal elements is 12 µm which results in a periodic spacing of 120 µm along the x- and y-axes. Other shapes of the features, e.g., disks, polygons, etc., and other placements of the features with respect to each other are possible.

Additionally in this example, an arrangement 345 of the patterned layers $L_1$, $L_2$, . . . , $L_N$ is such that each pair of adjacent patterned layers $L_j$, $L_{j+1}$ is separated by an axial offset $\Delta z>0$, where j=1, . . . , N−1. As such, a 3D lattice formed by the arrangement 345 of the patterned layers $L_1$, $L_2$, . . . , $L_N$ has a period along the z-axis equal to the axial offset $\Delta z$. In the example illustrated in FIG. 3, the axial offset $\Delta z$ of adjacent patterned layers $L_j$, $L_{j+1}$ patterned with the pattern P is of order 100 µm, e.g., between 50 µm and 200 µm. In some implementations, the axial offset $\Delta z$ is substantially equal to a thickness $t_{S(j+1)}$ of the $(j+1)^{th}$ substrate. In some implementations, the adjacent patterned layers $L_j$, $L_{j+1}$ is can be separated from each other through spacer elements of thickness $t_{SP}$. In such case, the axial offset $\Delta z$ is substantially equal to the sum of the thicknesses of the $(j+1)^{th}$ substrate and spacer elements $t_{S(j+1)}+t_{SP}$.

The arrangement 345 of the patterned layers $L_1$, $L_2$, . . . , $L_N$ is defined in FIG. 3 as (i) the pattern P of each of the patterned layers $L_1$, $L_2$, . . . , $L_N$ and (ii) the axial offset $\Delta z$ between each pair of adjacent patterned layers $L_j$, $L_{j+1}$. Moreover, parameters (i) and (ii) which define the arrangement 345 are specified such that the 3D lattice of patterned layers determined by the specified parameters is spectrally equivalent, over the wavelength range $[\lambda_{min},\lambda_{max}]$, to an optical spectrum w($\lambda$) 350. As described above in connection with FIG. 1, the optical spectrum w($\lambda$) 350 is associated with a characteristic to be measured. For example, if here the characteristic—to which the optical spectrum w($\lambda$) 350 is associated—is salinity, then the ICE 340 having the arrangement 345 of the patterned layers $L_1$, $L_2$, . . . , $L_N$ can be used as part of the optical analysis tool 110 to determine salinity of wellbore fluids 130.

Note that if the axial offset $\Delta z$ of the patterned layers $L_1$, $L_2$, . . . , $L_N$ is modified—e.g., by axially translating during operation of the ICE 340 each pair of adjacent patterned layers $L_i$, $L_{i+1}$ relative to each other by an axial offset $\Delta z' \neq \Delta z$—then a different 3D lattice of patterned layers is generated. The new axial offset $\Delta z'$ can be specified such that the different 3D lattice of patterned layers is spectrally equivalent, over the wavelength range $[\lambda_{min},\lambda_{max}]$, to another optical spectrum w'($\lambda$) (not shown in FIG. 3) associated with another characteristic to be measured. For example, if here the other characteristic—to which the optical spectrum w'($\lambda$) is associated—is mixing ratios, then the ICE 340 having the other arrangement of the patterned layers $L_1$, $L_2$, . . . , $L_N$ can be used as part of the optical analysis tool 110 to determine mixing ratios of wellbore fluids 130. In this manner, multiple optical spectra associated with multiple characteristics to be measured are available for weighting the sample modified light 135 that illuminates the ICE 340, during operation thereof.

In other implementations not shown in FIG. 3, constitutive electrically conductive materials of at least some adjacent patterned layers $L_j$, $L_{j+1}$ are different. For instance, every other patterned layers $L_j$ and $L_{j+2}$ can be printed with a pattern P on respective $j^{th}$ and $(j+2)^{th}$ substrates using Ag-based electrically conductive ink, while the in-between patterned layers $L_{j-1}$ and $L_{j+1}$ are printed with the pattern P on respective $(j-1)^{th}$ and $(j+1)^{th}$ substrates using Al-based electrically conductive ink. In this case, another 3D lattice formed by this arrangement of the patterned layers of the ICE 340 has a period $2\Delta z$ along the z-axis equal to twice the axial offset $\Delta z$ between adjacent patterned layers. Such other 3D lattice of patterned layers is spectrally equivalent, over the wavelength range $[\lambda_{min},\lambda_{max}]$, to another optical spectrum w($\lambda$) (not shown in FIG. 3) associated with another characteristic to be measured.

In some other implementations, axial offsets between at least some pairs of adjacent patterned layers $L_j$, $L_{j+1}$ are different. For instance, a pair of adjacent layers $L_j$ and $L_{j+1}$ patterned with pattern P can be separated by an axial offset $\Delta z$, while a subsequent pair of adjacent layers $L_{j+1}$ and $L_{j+2}$ patterned with pattern P are separated by a different axial offset $\Delta z' \neq \Delta z$. In this case, another 3D lattice formed by this arrangement of the patterned layers of the ICE 340 has a period $\Delta z + \Delta z'$ along the z-axis equal to the sum of the axial offset $\Delta z$ between the pair of adjacent patterned layers $L_j$ and $L_{j+1}$ and the axial offset $\Delta z'$ between the subsequent pair of adjacent patterned layers $L_{j+1}$ and $L_{j+2}$. Such other 3D lattice of patterned layers is spectrally equivalent, over the wavelength range $[\lambda_{min}, \lambda_{max}]$, to another optical spectrum w(λ) (not shown in FIG. 3) associated with another characteristic to be measured.

Many other 3D lattices of patterned layers can be generated by appropriately combining the above-noted different patterns (e.g., P, P', . . . ) of the layers of the ICE 340, different constitutive electrically conductive materials (e.g., Ag-based ink, Al-based ink, . . . ) of the patterned layers, different axial offsets (e.g., $\Delta z$, $\Delta z'$, . . . ) between adjacent patterned layers, etc., as long as some translational symmetry is maintained along the z-axis of each of such arrangements of the patterned layers of the ICE 340. Each of these other 3D lattices of patterned layers is spectrally equivalent, over the wavelength range $[\lambda_{min}, \lambda_{max}]$, to a corresponding optical spectrum w(λ) (not shown in FIG. 3) associated with another characteristic to be measured.

Arrangements of multiple frequency selective surfaces of an ICE were described above that result in either Moiré patterns of superimposed patterned layers or 3D lattices of patterned layers that are spectrally equivalent with respective characteristics to be measured.

Figure 4:
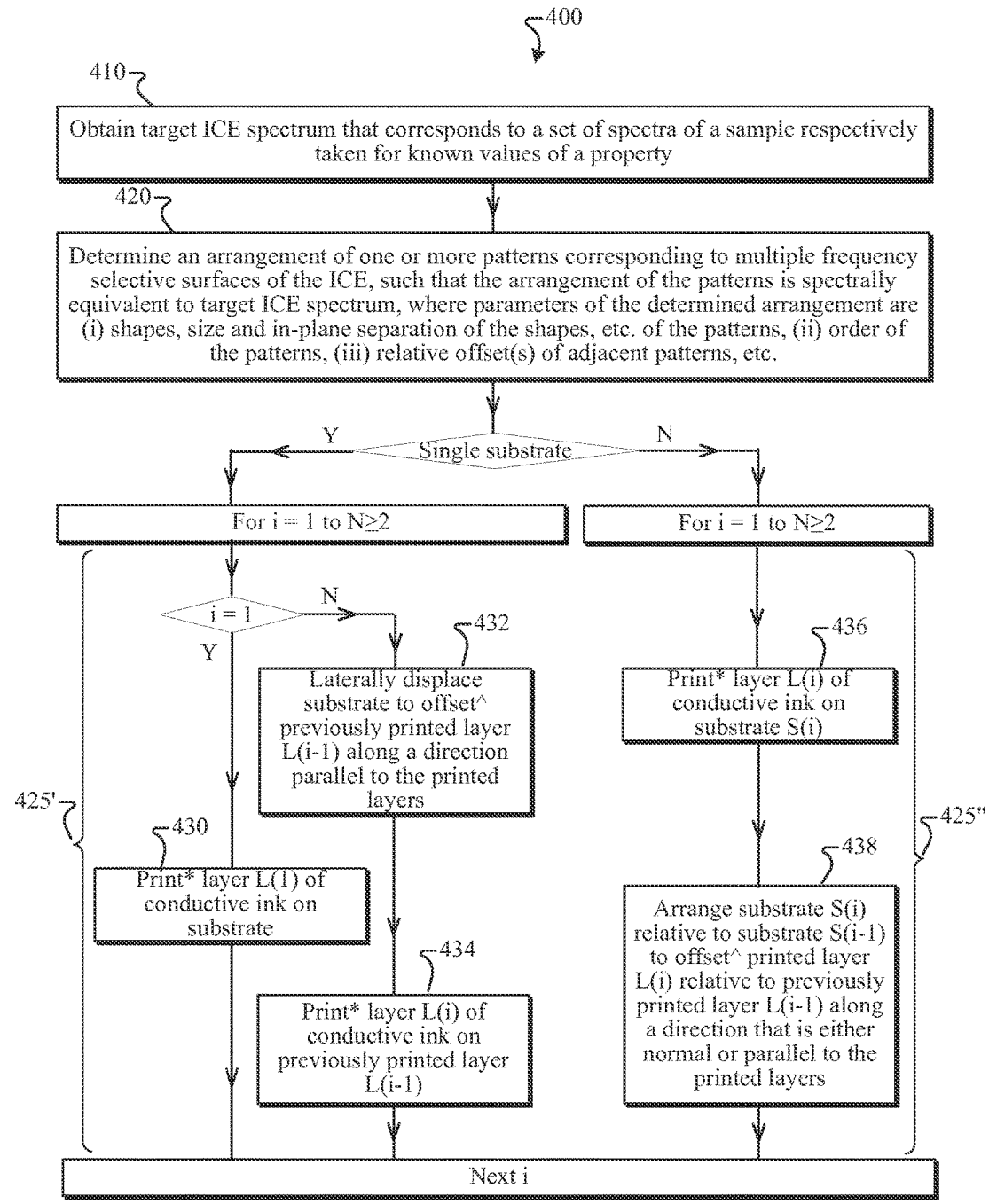
FIG. 4 is a flow chart of a process for fabricating an ICE that contains multiple frequency selective surfaces, where the frequency selective surfaces are printed using electrically conductive inks.

FIG. 4 is a flow chart of a process 400 for fabricating an ICE that contains multiple frequency selective surfaces, where the frequency selective surfaces are printed using electrically conductive inks. The process 400 can be used to fabricate the ICE 104, 240-a, 240-b, 240-c or 340 described above in connection with FIGS. 1, 2A-2C and 3.

At 410, a target ICE spectrum associated with a characteristic of a sample is obtained. The obtained target ICE spectrum corresponds to a set of spectra of the sample, where the spectra were respectively taken for known values of the characteristic of the sample. The characteristic can be any one of multiple physical or chemical properties of the sample including concentration of a given substance in the sample, a gas-oil-ratio (GOR), pH value, density, viscosity, etc. Moreover, the obtained target ICE spectrum can be any of the optical spectra w(λ) 150, 250-a, 250-b, 250-c or 350 described above.

At 420, an arrangement of one or more patterns corresponding to the multiple frequency selective surfaces of the ICE is determined to be spectrally equivalent to the target ICE spectrum obtained at 410. Parameters of the determined arrangement are (i) shapes, size, in-plane separation, etc. of the shapes associated with the one or more patterns, (ii) order of the patterns, (iii) relative lateral and/or axial offset(s) of adjacent patterns, etc.

Various algorithms can be used to determine, from among many combinations of the parameters (i), (ii), (iii), etc., a parameter combination corresponding to an arrangement of the multiple frequency selective surfaces of the ICE that is spectrally equivalent to the target ICE spectrum. In some implementations, an initial guess of values of the parameter combination is made and an electromagnetic simulation is performed to find a resulting spectrum for the current guessed values of the parameters. The results are compared with the target ICE spectrum and new parameter values are computed in an attempt to find parameters for which an error between the target ICE spectrum and a resultant spectrum is minimized. Any conventional multivariate minimization scheme, such as conjugate gradient, steepest descent, Levenberg—Marquart, and the like, can be used. Several conventional computational methods can be used to generate a spectrum for a given parameter combination, such as periodic method of moments, or the finite difference time domain (FDTD) method.

As described above in connection with Equations (3) and (6), Moiré patterns have one or more features that are larger than the pattern features of a single frequency selective surface. In this manner, Moiré patterns (e.g., described above in connection with FIGS. 2A-2C) or 3D lattices of patterned layers (e.g., described above in connection with FIG. 3) corresponding to some of the arrangements of the multiple frequency selective surfaces of the ICE determined at 420 are spectrally equivalent to a target ICE spectrum over longer wavelengths (or equivalently lower frequencies) than conventional ICEs that use a single frequency selective surface.

In some implementations of the disclosed technologies, a wavelength range $[\lambda_{min}, \lambda_{max}]$ over which an arrangement of the frequency selective surfaces of the ICE is determined at 420 to be spectrally equivalent to the target ICE spectrum extends through an IR (2.5-200 μm) spectral range. For example, the wave number range 4000-1000 cm$^{-1}$ (corresponding to ~15-60 μm in wavelength) of the IR spectroscopic spectrum is known as the functional group region. The functional group region—corresponding to the IR active polar covalent molecular bonds in organic molecules, such as hydrocarbons—provides the most useful information in IR spectrum. In some implementations of the disclosed technologies, the wavelength range $[\lambda_{min}, \lambda_{max}]$ over which another arrangement of the frequency selective surfaces of the ICE is determined at 420 to be spectrally equivalent to the target ICE spectrum extends through a microwave (0.2-10 mm) spectral range.

In some cases, it can be determined at 420 that an arrangement of the multiple frequency selective surfaces of the ICE that causes a Moiré pattern from superimposed patterned layers is spectrally equivalent to the target ICE spectrum. Further in these cases, it is determined that the Moiré pattern is generated when the patterned layers are laterally translated and/or rotated with respect to each other by particular lateral offset(s) δx and/or δθ, but have no axial separation between adjacent patterned layers, δz=0. One such case is the arrangement 245-a of the frequency selective surfaces of the ICE 240-a described above in connection with FIG. 2A, when the axial offset δz=0. Another such case is the arrangement 245-b of the frequency selective surfaces of the ICE 240-b described above in connection with FIG. 2B. Other such cases are the arrangements 245', 245" and 245''' of the frequency selective surfaces of the ICE 240-c described above in connection with FIG. 2C, when the axial offset δz=0. Such arrangements of the multiple frequency selective surfaces of the ICE are fabricated by patterning a first of the multiple layers on a single transparent substrate, and by patterning the remaining ones of the multiple layers directly onto respective previously patterned layer. The process 400 can be used to address the foregoing cases in the following manner.

If a single substrate is to be used for fabricating the multiple frequency selective surfaces of the ICE, then a loop 425' will be executed after 420. Each iteration "i" of the loop 425' is used to fabricate a frequency selective surface as a layer $L_i$ of conducting material patterned in accordance with a corresponding pattern $P_i$ obtained at 420.

At 430, a first layer $L_1$ is printed on a substrate in accordance with a first pattern $P_1$. The substrate is made from an insulating, transparent material, e.g., acetate. A thickness of the substrate is selected, among other things, to provide a desired flexibility and/or robustness to the ICE.

An electrically conductive ink is used to print an $i^{th}$ layer $L_i$ (including the first layer $L_1$), where i=1, ... N. For example, the electrically conductive ink can include any metallic (e.g., Ag, Au, etc.) flakes. As another example, the electrically conductive ink includes graphite. As yet another example, the electrically conductive ink includes conductive polymers. Although optical properties of the $i^{th}$ frequency selective surface depend on the pattern $P_i$, used for printing the $i^{th}$ layer $L_i$, and the morphology of the $i^{th}$ layer $L_i$, where i=1, ... N, the optical properties are independent of a thickness $t_i$ of the $i^{th}$ layer $L_i$, as long the thickness exceeds the skin depth over a desired wavelength range $[\lambda_{min}, \lambda_{max}]$.

High-resolution inkjet printers are used to print the ith layer $L_i$, where i=1, ... N. Table 1 lists resolutions of commercially available inkjet printers and the corresponding printable pattern feature sizes.

TABLE 1

| | Resolution (dot-per-inch) | | | | | |
|---|---|---|---|---|---|---|
| | 600 | 720 | 1200 | 2400 | 4800 | 9600 |
| Pattern feature size (μm) | 42.33 | 35.28 | 21.17 | 10.58 | 5.29 | 2.65 |

Table 1 indicates that commercially available inkjet printers are capable of printing patterns, such as the ones illustrated in FIGS. 2A-2C or 3 onto the substrate as in the case of the first layer $L_1$, and directly onto previously printed layers $L_i$, where 2≤i≤N. Patterning the layers $L_1$, ..., $L_N$ using commercially available inkjet printers and conducting inks is economically advantageous relative to conventionally patterning the layers using lithography.

For all subsequent layers $L_i$, where 2≤i≤N, an $i^{th}$ layer $L_i$ is printed using conducting ink in the following manner.

In some implementations, at 432, the substrate is laterally offset in accordance with a corresponding relative offset $\delta x_i$ or $\delta\theta_i$ determined at 420, to laterally offset the $(i-1)^{th}$ layer $L_{i-1}$ printed during the previous iteration "i−1" of the loop 425'. In this case, at 434, the $i^{th}$ layer $L_i$ is printed, in accordance with an $i^{th}$ pattern $P_i$, onto the previously printed $(i-1)^{th}$ layer $L_{i-1}$ that was offset at 432.

In other implementations, at 432 (not shown in FIG. 4), an $i^{th}$ offset pattern $P_i'$ is determined by offsetting an $i^{th}$ pattern $P_i$ obtained at 420. In this other case, at 434 (not shown in FIG. 4), the $i^{th}$ layer $L_i$ is printed, in accordance with the $i^{th}$ offset pattern $P_i'$ determined at 432, onto the $(i-1)^{th}$ layer $L_{i-1}$ printed during the previous iteration "i−1" of the loop 425'.

Remaining layers $L_{i+1}$, ..., $L_N$ of the ICE will be fabricated using additional iterations of the loop 425'.

Returning to 420, in some other cases, it can be determined that an arrangement of the multiple frequency selective surfaces of the ICE that causes a Moiré pattern from superimposed patterned layers or a 3D lattice of patterned layers is spectrally equivalent to the target ICE spectrum. For example, it can be determined that the Moiré pattern is generated when the patterned layers are offset with respect to each other not only by a particular lateral offset(s) $\delta x > 0$ and/or $\delta\theta > 0$, but also by a finite (non-zero) axial offset $\delta z > 0$ between adjacent patterned layers. One such case is the arrangement 245-a of the frequency selective surfaces of the ICE 240-a described above in connection with FIG. 2A, when the axial offset is non-zero, $\delta z > 0$. Other such cases are the arrangements 245', 245" and 245'" of the frequency selective surfaces of the ICE 240-c described above in connection with FIG. 2C, when the axial offset is non-zero, $\delta z > 0$. As another example, it can be determined that adjacent patterned layers of the 3D lattice of patterned layers are axially separated by a particular, finite (non-zero) axial offset $\delta z > 0$. One such case is the arrangement 345 of the frequency selective surfaces of the ICE 340 described above in connection with FIG. 3.

Such arrangements of the multiple frequency selective surfaces of the ICE are fabricated by patterning multiple layers on respective a transparent substrates. The process 400 can be used to address the foregoing cases in the following manner.

If multiple substrates are to be used for fabricating the multiple frequency selective surfaces of the ICE, then a loop 425" will be executed after 420. Each iteration "i" of the loop 425" is used to fabricate a frequency selective surface as layer $L_i$ of conducting material patterned on a respective $i^{th}$ substrate in accordance with a corresponding pattern $P_i$ obtained at 420.

At 436, an $i^{th}$ layer $L_i$ is printed on an $i^{th}$ substrate in accordance with an $i^{th}$ pattern $P_i$. As noted above, a thickness of the $i^{th}$ substrate is selected, among other things, to provide a desired flexibility and/or robustness to the ICE. Further as noted above, an electrically conductive ink is used to print the $i^{th}$ layer $L_i$ with commercially available inkjet printers, for instance.

At 438, the $i^{th}$ substrate is arranged relative to an adjacent $(i-1)^{th}$ substrate to offset, by an $i^{th}$ lateral offset (e.g., $\delta x_i$ or $\delta\theta_i$) or an $i^{th}$ axial offset (e.g., $\delta z_i$), the $i^{th}$ layer $L_i$ printed on the $i^{th}$ substrate at 436 relative an $(i-1)^{th}$ layer $L_{i-1}$ previously printed on the adjacent $(i-1)^{th}$ substrate during the previous iteration "i−1" of the loop 425".

Remaining layers $L_{i+1}$, ..., $L_N$ of the ICE will be fabricated using additional iterations of the loop 425".

Figure 5A:
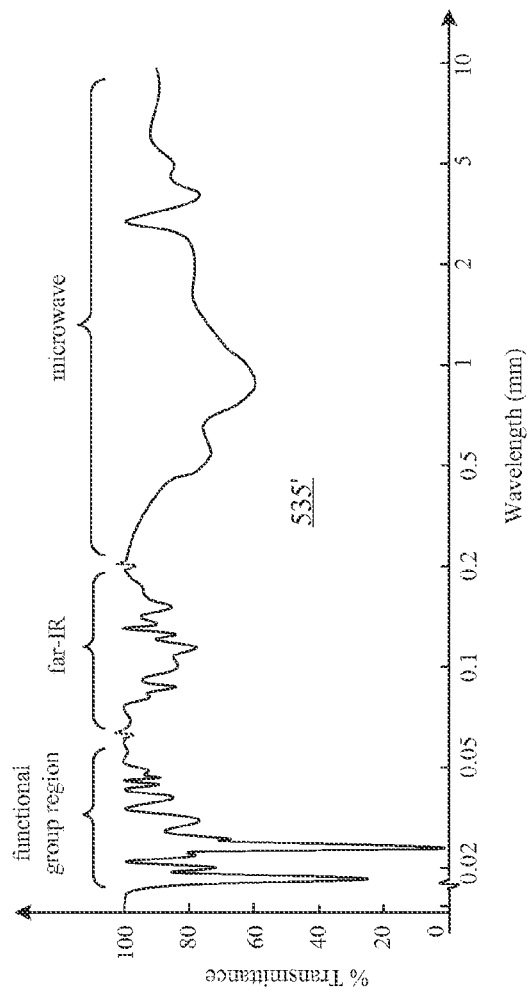
FIGS. 5A-5C show various configurations of an example of a system for analyzing wellbore fluids that uses a well logging tool including an ICE that contains multiple frequency selective surfaces.
Figure 5A:
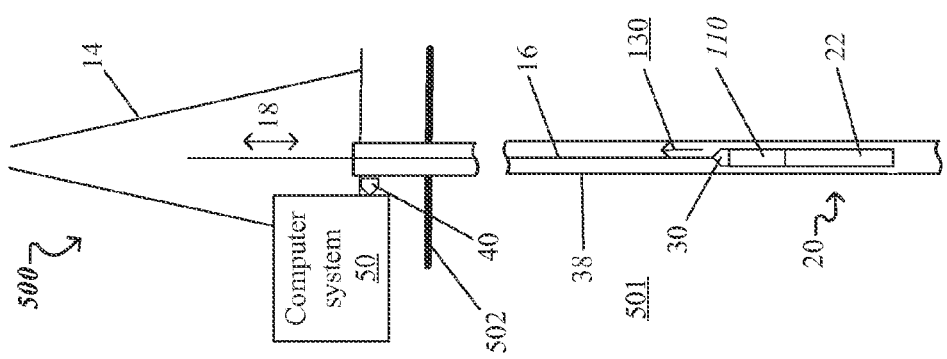
Figure 5B:
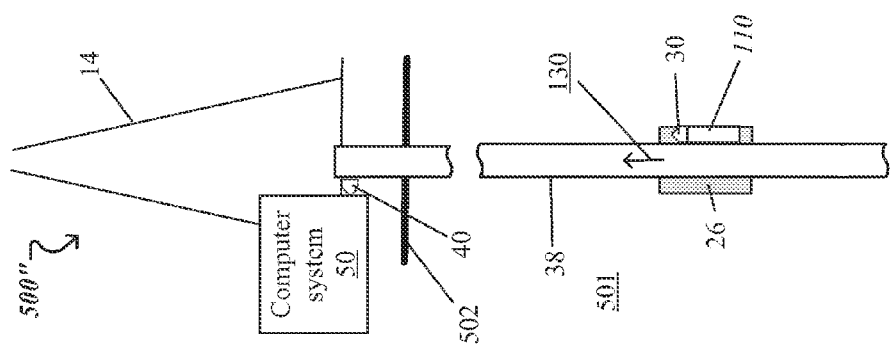
Figure 5C:
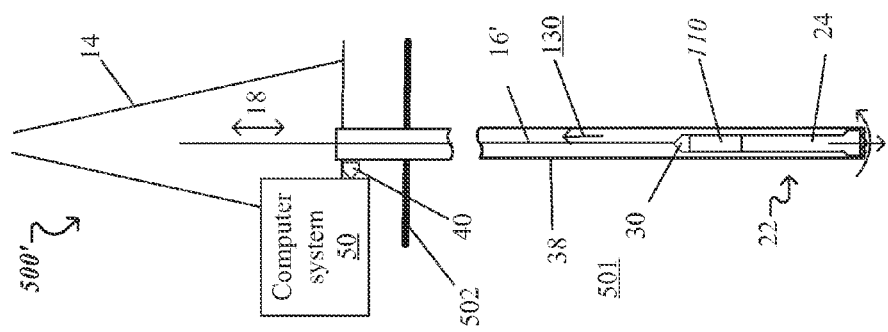

FIGS. 5A-5C show multiple configurations 500, 500', 500" of an example of a system for analyzing wellbore fluids 130, such that analyses are generated from at least some measurements taken with an optical analysis tool 110, which includes an ICE that contains multiple frequency selective surfaces, as the one described above in connection with FIG. 1. Here, the optical analysis tool 110 is referred to as a well logging tool 110, and the disclosed system is referred to as a well logging system.

Each of the configurations 500, 500', 500" of the well logging system illustrated in FIGS. 5A-5C includes a rig 14 above the ground surface 502 and a wellbore 38 below the ground surface. The wellbore 38 extends from the ground surface into the earth 501 and generally passes through multiple geologic formations. In general, the wellbore 38 can contain wellbore fluids 130. The wellbore fluids 130 can be crude petroleum, mud, water or other substances and combinations thereof. Moreover, the wellbore fluids 130 may be at rest, or may flow toward the ground surface 502, for instance. Additionally, surface applications of the well logging tool 110 may include water monitoring and gas and crude transportation and processing.

FIG. 5A shows a configuration 500 of the well logging system which includes a tool string 20 attached to a cable 16 that can be lowered or raised in the wellbore 38 by draw works 18. The tool string 20 includes measurement and/or logging tools to generate and log information about the wellbore fluids 130 in the wellbore 38. In the configuration 500 of the well logging system, this information can be generated as a function of a distance (e.g., a depth) with respect to the ground surface 502. In the example illustrated in FIG. 5A, the tool string 20 includes the well logging tool 110, one or more additional well logging tool(s) 22, and a telemetry transmitter 30. Each of the well logging tools 110 and 22 measures one or more characteristics of the wellbore fluids 130. In some implementations, the well logging tool 110 determines values of the one or more characteristics in real time and reports those values instantaneously as they occur in the flowing stream of wellbore fluids 130, sequentially to or simultaneously with other measurement/logging tools 22 of the tool string 20.

FIG. 5B shows another configuration 500' of the well logging system which includes a drilling tool 24 attached to a drill string 16'. The drilling tool 24 includes a drill bit 26, the ICE-based well logging tool 110 configured as a measurement while drilling (MWD) and/or logging while drilling (LWD) tool, and the telemetry transmitter 30. Drilling mud is provided through the drill string 16' to be injected into the borehole 38 through ports of the drill bit 26. The injected drilling mud flows up the borehole 38 to be returned above the ground level 502, where the returned drilling mud can be resupplied to the drill string 16' (not shown in FIG. 5B). In this case, the MWD/LWD-configured well logging tool 110 generates and logs information about the wellbore fluids 130 (e.g., drilling mud in this case) adjacent the working drill bit 26.

FIG. 5C shows yet another configuration 500" of the well logging system which includes a permanent installation adjacent to the borehole 38. In some implementations, the permanent installation is a set of casing collars that reinforce the borehole 38. In this case, a casing collar 28 from among the set of casing collars supports the well logging tool 110 and the telemetry transmitter 30. In this manner, the well logging tool 110 determines and logs characteristics of the wellbore fluids 130 adjacent the underground location of the casing collar 28.

In each of the above configurations 500, 500' and 500" of the well logging system, the values of the one or more characteristics measured by the well logging tool 110 are provided (e.g., as a detector signal 165) to the telemetry transmitter 30. The latter communicates the measured values to a telemetry receiver 40 located above the ground surface 502. The telemetry transmitter 30 and the telemetry receiver 40 can communicate through a wired or wireless telemetry channel. In some implementations of the system configurations 500, 500' illustrated in FIGS. 5A and 5B, e.g., in slickline or coiled tubing applications, measurement data generated by the well logging tool 110 can be written locally to memory of the well logging tool 110.

The measured values of the one or more characteristics of the wellbore fluids 130 received by the telemetry receiver 40 can be logged and analyzed by a computer system 50 associated with the rig 14. In this manner, the measurement values provided by the well logging tool 110 can be used to generate physical and chemical information about the wellbore fluids 130 in the wellbore 38.

Characteristics of the wellbore fluids 130 that can be related to one or more spectral regions (e.g., functional group region, far-IR, microwave, etc.) of the spectrum 535' of the sample modified light through optical spectra associated with any one of the ICEs 140, 240-a, 240-b, 240-c or 340 are concentrations of one of asphaltene, saturates, resins, aromatics; solid particulate content; hydrocarbon composition and content; gas composition C1-C6 and content: $CO_2$, $H_2S$ and correlated PVT properties including GOR, bubble point, density; a petroleum formation factor; viscosity; a gas component of a gas phase of the petroleum; total stream percentage of water, gas, oil, solid articles, solid types; oil finger printing; reservoir continuity; oil type; and water elements including ion composition and content, anions, cations, salinity, organics, pH, mixing ratios, tracer components, contamination, or other hydrocarbon, gas, solids or water property.

Some embodiments have been described in detail above, and various modifications are possible. While this specification contains many specifics, these should not be construed as limitations on the scope of what may be claimed, but rather as descriptions of features that may be specific to particular embodiments. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the embodiments described above should not be understood as requiring such separation in all embodiments.

Other embodiments fall within the scope of the following claims.

What is claimed is:

1. A measurement tool for measuring a characteristic of a sample, the measurement tool comprising: an integrated computational element (ICE) comprising a plurality of layers stacked along a first axis, wherein each of the layers has a plane perpendicular to the first axis, the layers being laterally offset from each other along the first axis, and a constitutive material of each of the layers being electrically conductive and patterned with a corresponding pattern, wherein an arrangement of the patterns with respect to each other is related to a characteristic of a sample, wherein the plurality of layers of the ICE comprises a first layer of electrically conductive material patterned with a first pattern and a second layer of electrically conductive material patterned with a second pattern, and the arrangement of the first and second patterns with respect to each other comprises the lateral offset in the plane perpendicular to the first axis, such that the offset causes a Moiré pattern related to the characteristic of the sample.

2. The measurement tool of claim 1, wherein the lateral offset comprises a translation or a rotation in the plane perpendicular to the first axis.

3. The measurement tool of claim 1, wherein the first pattern is substantially the same as the second pattern.

4. The measurement tool of claim 3, wherein a pattern difference between the first and second patterns is less than a target pattern difference.

5. The measurement tool of claim 1, wherein
the plurality of layers of the ICE comprises three or more layers of electrically conductive material, and
the arrangement of the patterns of the three or more layers of material with respect to each other has translational symmetry along the first axis to form a three dimensional (3D) lattice of the patterns, such that the 3D lattice is related to the characteristic of the sample.

6. The measurement tool of claim 5, wherein the constitutive electrically conductive materials of the three or more layers are patterned with a same pattern.

7. The measurement tool of claim 5, wherein the three or more layers comprise
a first layer of electrically conductive material patterned with a first pattern,
a third layer of electrically conductive material patterned with a third pattern, and
a second layer of electrically conductive material between the first and third layers, the second layer being patterned with a second pattern different from the first pattern.

8. The measurement tool of claim 7, wherein a separation between the first and second patterns is different from a separation between the second and third patterns.

9. The measurement tool of claim 7, wherein the third pattern is the same as the first pattern.

10. The measurement tool of claim 5, wherein the constitutive electrically conductive material of at least some adjacent layers are different materials.

11. The measurement tool of claim 1, wherein the ICE comprises one or more substrates, wherein the substrates of the ICE are formed from materials that are transparent to light in at least a portion of a wavelength range.

12. The measurement tool of claim 11, wherein adjacent layers of the ICE are separated by a respective one of the substrates.

13. The measurement tool of claim 11, wherein
a first layer of the ICE is patterned on a surface of a single substrate, and
remaining layers of the ICE are patterned on a surface of a respective previous layer.

14. The measurement tool of claim 11, wherein each pattern of the constitutive electrically conductive materials of the plurality of layers comprises the same features forming a periodic array associated with the pattern and arranged parallel to the one or more substrates.

15. The measurement tool of claim 14, wherein the features each comprise one or more geometric shapes selected from the group consisting of polygons and circles.

16. The measurement tool of claim 14, wherein the constitutive electrically conductive materials of the layers of the ICE comprise one or more electrically conductive inks.

17. The measurement tool of claim 16, wherein the one or more electrically conductive inks comprise metal flakes.

18. The measurement tool of claim 17, wherein the metal flakes comprise silver or gold.

19. The measurement tool of claim 16, wherein the one or more electrically conductive inks comprise graphite or conductive polymers.

20. A method comprising:
printing the patterns associated with the layers of the ICE of the measurement tool of claim 18 on the one or more substrates of the ICE using the one or more electrically conductive inks.

21. The method of claim 20, wherein said printing of the electrically conductive ink patterns on the respective separator substrates is performed using a jet printer.

22. The method of claim 20, wherein said printing of the electrically conductive ink patterns on the respective separator substrates is performed using micro-contact printing with a stamp.

23. The measurement tool of claim 1, wherein the arrangement of the patterns causes the ICE to selectively transmit or reflect, during operation of the measurement tool, light in at least a portion of a wavelength range by differing amounts, the differing amounts being related to the characteristic of the sample.

24. The measurement tool of claim 23, wherein
the wavelength range comprises a first wavelength sub-range and a second wavelength sub-range adjacent to the first wavelength sub-ranged, and
the arrangement of the patterns comprises
a first arrangement of the patterns that causes the ICE to selectively transmit or reflect, during operation of the measurement tool, light in the first wavelength sub-range by first differing amounts, and
a second arrangement of the patterns that causes the ICE to selectively transmit or reflect, during operation of the measurement tool, light in the second wavelength sub-range by second differing amounts, such that a combination of the first differing amounts over the first wavelength sub-range and the second differing amounts over the second wavelength sub-range is related to the characteristic of the sample.

25. The measurement tool of claim 24, wherein wavelengths in the first wavelength sub-range are shorter than wavelengths in the second wavelength sub-range.

26. The measurement tool of claim 24, wherein the combination is a weighted sum of the first differing amounts over the first wavelength sub-range and the second differing amounts over the second wavelength sub-range.

27. The measurement tool of claim 24, wherein the light is reflected or transmitted concurrently by the first and second arrangements of patterns.

28. The measurement tool of claim 24, wherein the light is reflected or transmitted sequentially by the first and second arrangements of patterns.

29. The measurement tool of claim 23, wherein the wavelength range comprises wavelengths from 15 μm to 10 mm.

30. The measurement tool of claim 23, further comprising:
a light source positioned to illuminate the sample with light having a first spectrum over the wavelength range, wherein the ICE is positioned to receive light from the sample in response to the illumination, such that the light received from the sample has a second spectrum over the wavelength range, the second spectrum corresponding to the first spectrum modified by the sample; and
an optical transducer positioned to receive light from the ICE and produce a signal having a value related to an integrated intensity of the light from the ICE across the wavelength range, wherein the signal value corresponds to a value of the property of the sample.

31. The measurement tool of claim 1, wherein the sample comprises wellbore fluids and the characteristic of the sample is a property of the wellbore fluids.

32. The measurement tool of claim 31, wherein the property of the sample is selected from the group consisting of a concentration of a substance in the sample, a pH of the sample, a ratio of concentrations of two different substances in the sample, a density of the sample, and a viscosity of the sample.

33. A method comprising:
placing the measurement tool of claim 31, in a wellbore; and
determining the value of a property of a sample in the wellbore using the measurement tool of claim 31.

\* \* \* \* \*

UNITED STATES PATENT AND TRADEMARK OFFICE
CERTIFICATE OF CORRECTION

PATENT NO. : 9,708,908 B2
APPLICATION NO. : 14/762194
DATED : July 18, 2017
INVENTOR(S) : Li Gao et al.

It is certified that error appears in the above-identified patent and that said Letters Patent is hereby corrected as shown below:

In the Specification

In Column 5, Line 23, after "value of the concentration" delete "$C_X$" and please insert --$c_X$--

Signed and Sealed this
Twentieth Day of February, 2018

Andrei Iancu
*Director of the United States Patent and Trademark Office*